(12) United States Patent
Dubrul et al.

(10) Patent No.: US 6,602,204 B2
(45) Date of Patent: Aug. 5, 2003

(54) INTRAOPERATIVE TISSUE TREATMENT METHODS

(75) Inventors: William R. Dubrul, Redwood City, CA (US); Richard E. Fulton, Grand Junction, CO (US); Robert M. Curtis, Hillsborough, CA (US)

(73) Assignee: Artemis Medical, Inc, Hayward, CA (US)

( * ) Notice: Subject to any disclaimer, the term of this patent is extended or adjusted under 35 U.S.C. 154(b) by 0 days.

(21) Appl. No.: 09/844,661

(22) Filed: Apr. 27, 2001

(65) Prior Publication Data

US 2002/0019597 A1 Feb. 14, 2002

Related U.S. Application Data

(63) Continuation-in-part of application No. 09/588,278, filed on Jun. 5, 2000, now Pat. No. 6,530,923, and a continuation-in-part of application No. 09/336,360, filed on Jun. 18, 1999, now Pat. No. 6,270,464, which is a continuation-in-part of application No. 09/248,088, filed on Feb. 9, 1999, now Pat. No. 6,221,006.

(60) Provisional application No. 60/200,546, filed on Apr. 27, 2000, provisional application No. 60/154,394, filed on Sep. 17, 1999, provisional application No. 60/146,892, filed on Aug. 2, 1999, provisional application No. 60/137,775, filed on Jun. 4, 1999, provisional application No. 60/117,421, filed on Jan. 27, 1999, provisional application No. 60/114,863, filed on Jan. 6, 1999, provisional application No. 60/105,284, filed on Oct. 22, 1998, provisional application No. 60/092,734, filed on Jul. 14, 1998, provisional application No. 60/090,243, filed on Jun. 22, 1998, and provisional application No. 60/074,199, filed on Feb. 10, 1998.

(51) Int. Cl.[7] ............................................. A61B 10/00
(52) U.S. Cl. ..................................................... 600/567
(58) Field of Search .............................. 600/567, 431, 600/432, 436; 604/13, 19; 606/1, 41, 117, 113–115; 128/899

(56) References Cited

U.S. PATENT DOCUMENTS

| | | | |
|---|---|---|---|
| 3,996,938 A | 12/1976 | Clark, III | |
| 4,650,466 A | 3/1987 | Luther | |
| 4,799,495 A | 1/1989 | Hawkins et al. | |
| 5,183,463 A | 2/1993 | Debbas | |
| 5,221,269 A | 6/1993 | Miller et al. | |
| 5,709,697 A | 1/1998 | Ratcliff et al. | |
| 5,795,308 A | 8/1998 | Russin | |
| 6,053,876 A | 4/2000 | Fisher | |
| 6,161,034 A | 12/2000 | Burbank et al. | |
| 6,238,412 B1 | 5/2001 | Dubrul et al. | |
| 6,356,782 B1 * | 3/2002 | Sirimanne et al. | 128/899 |
| 6,375,634 B1 * | 4/2002 | Carroll | 604/13 |
| 2002/0007130 A1 | 1/2002 | Burbank et al. | |
| 2002/0016555 A1 | 2/2002 | Ritchart et al. | |
| 2002/0019640 A1 | 2/2002 | McGuckin, Jr. | |
| 2002/0026201 A1 | 2/2002 | Foerster et al. | |

FOREIGN PATENT DOCUMENTS

| | | |
|---|---|---|
| EP | 0 983 749 A2 | 3/2000 |
| WO | WO99/44506 | 9/1999 |
| WO | WO00/12009 | 3/2000 |
| WO | WO00/12010 | 3/2000 |

* cited by examiner

*Primary Examiner*—Max F. Hindenburg
*Assistant Examiner*—Brian Szmal
(74) *Attorney, Agent, or Firm*—James F. Hann; Haynes Beffel & Wolfeld LLP

(57) ABSTRACT

Intraoperative tissue treatment methods are used following the removal of target tissue, e.g. diseased tissue, from a target site, e.g. within a patient's breast, leaving access to the target site. In one method an expandable element is introduced into and expanded within a void at the target site. If all of the target tissue was not removed, then a layer of tissue at least partially surrounding the expanded element is removed from the patient, preferably in a substantially intact form. In a second method the suction inlet of a suction device is in fluid communication with the void. If all of the target tissue has not been removed, at least a portion of the collapsed tissue is removed from the patient and analyzed. With a third method, a flexible implant is passed through the sheath and into the void to at least substantially fill the void.

35 Claims, 18 Drawing Sheets

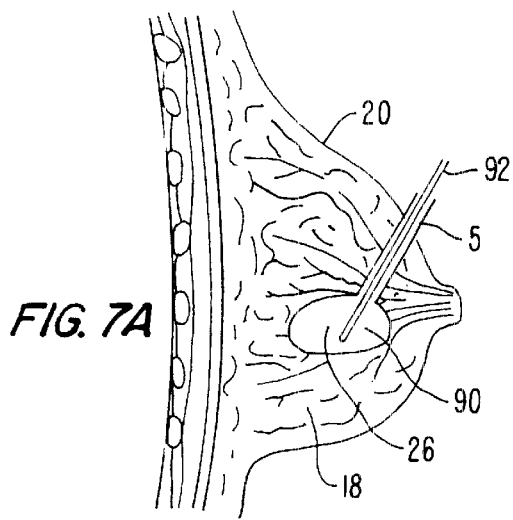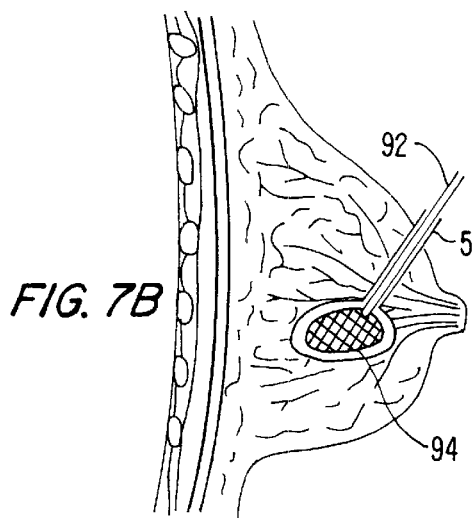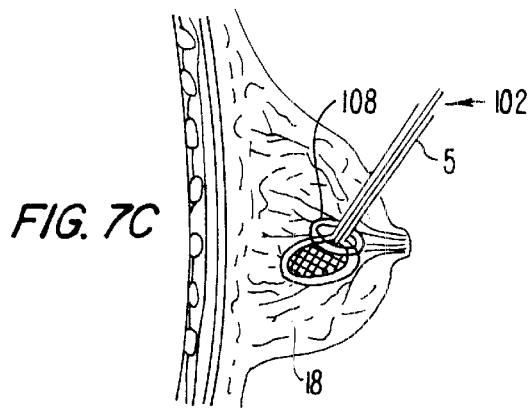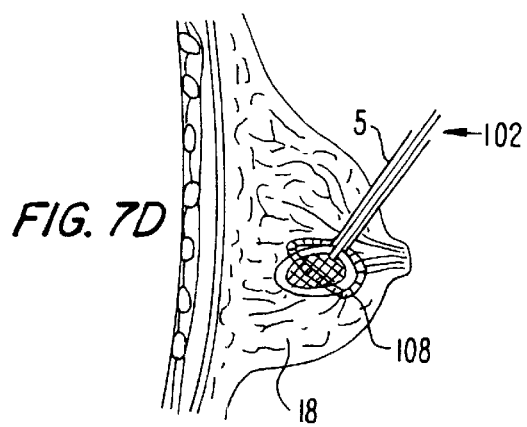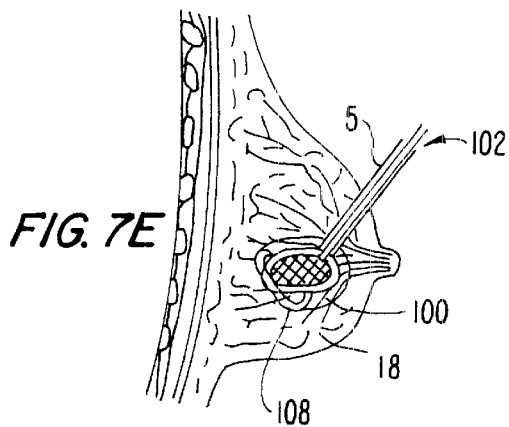

INTRAOPERATIVE TISSUE TREATMENT METHODS

CROSS-REFERENCES TO RELATED APPLICATIONS

This claims the benefit of Provisional Application No. 60/200,546 filed Apr. 27, 2000 and entitled DIAGNOSTIC AND THERAPEUTIC APPARATUSES AND METHODS FOR USE.

This is a continuation-in-part of the U.S. patent application Ser. No. 09/588,278 filed Jun. 5, 2000 now U.S. Pat. No. 6,530,923. U.S. Pat. No. 6,530,923 claims the benefit of the following provisional patent applications: Provisional Application No. 60/137,775 filed Jun. 4, 1999 and entitled TISSUE REMOVAL APPARATUS AND METHOD FOR USE; Provisional Application No. 60/146,892 filed Aug. 2, 1999 entitled DISEASE PREVENTING SHEATH APPARATUS AND METHODS FOR USE; Provisional Application No. 60/200,546 filed Apr. 27, 2000 and entitled DIAGNOSTIC AND THERAPEUTIC APPARATUSES AND METHODS FOR USE; Provisional Application No. 60/154,394 filed Sep. 17, 1999 and entitled ONCOLOGICAL APPARATUS AND METHOD FOR USE. U.S. Pat. No. 6,530,923 is also a continuation-in-part of U.S. patent application Ser. No. 09/336,360 filed Jun. 18, 1999 now U.S. Pat. No. 6,290,464 entitled BIOPSY LOCALIZATION METHOD AND DEVICE, which application claims priority from the following provisional applications:

Application No. 60/090,243, filed Jun. 22, 1998;

Application No. 60/092,734, filed Jul. 14, 1998;

Application No. 60/114,863, filed Jan. 6, 1999; and

Application No. 60/117,421, filed Jan. 27, 1999.

U.S. Pat. No. 6,530,923 is also a continuation-in-part of U.S. patent application Ser. No. 09/248,088 filed Feb. 9, 1999, now U.S. Pat. No. 6,221,006 which application claims benefit of the following provisional applications:

Application No. 60/074,199 filed Feb. 10, 1998; and

Application No. 60/105,284 filed Oct. 22, 1998.

BACKGROUND OF THE INVENTION

The M.D. Anderson Cancer Center in Houston, Tex. predicts that cancer will become the leading cause of death in the United States by the year 2002. Cancer presently results in over one thousand five hundred deaths every day in the United States (550,000 deaths every year). Therapy modalities for cancer are plentiful and continued to be researched with vigor. Still, the preferred treatment continues to be physical removal of the cancer. When applicable, surgical removal is preferred (breast, colon, brain, lung, kidney, etc.). Open, excisional, surgical removal is often extremely invasive so that efforts to remove cancerous tissue in less invasive ways continue, but have not yet been perfected.

The only cure for cancer continues to be the early diagnosis and subsequent early treatment. As cancer therapies continue at earlier stages of diagnosis, the cancerous tissue being operated on is also smaller. Early removal of the smaller cancers demand new techniques for removal and obliteration of these less invasive cancers.

There are a variety of techniques that attempt to accomplish less invasive cancer therapy, but so far without sufficiently improved results. For example, the ABBI system from U.S. Surgical Corporation and the Site Select system from ImaGyn Corporation, attempt to accomplish less invasive cancer therapy. However, conventional techniques require more than Minimally Invasive Surgery (MIS) techniques in that they require a large core (that is more than about 15 mm diameter) incision. Additionally, the Mammotome system from Johnson and Johnson and MIBB system from U.S. Surgical Corporation also require large core (over about 4 mm diameter) access to accomplish biopsy.

A recent convention held by the American Society of Surgical Oncologists on Mar. 13, 2000 reported that conventional stereotactic core biopsy (SCB) procedures fall short in providing definitive answers to detail precise surgical regimens after this SCB type vacuum assisted biopsy, especially with ductile carcinoma in situ (DCIS). Apparently these percutaneous systems damage "normal" tissue cells so that it is difficult to determine if the cells are "normal damaged" cells or early pre-cancerous (e.g. Atypical Ductal Hyperplasia (ADH)) cells.

A study presented by Dr. Ollila et al. from the University of North Carolina, Chapel Hill, demonstrated that histology and pathology is compromised using these conventional techniques because of the damage done to the removed tissue specimens. Hence, for many reasons, including the fact that DCIS is becoming more detectable and hence more prevalent in breast cancer diagnosis in the U.S., there is a growing need to improve upon conventional vacuum assisted core biopsy systems.

SUMMARY OF THE INVENTION

Broadly, the present invention is directed to procedures, including biopsy and tumorectomy methods, and associated apparatus which provide for less invasive techniques while also providing for enhanced tissue specimens being retrieved.

A first aspect of the invention is directed to an intraoperative tissue treatment method for use following the removal of target tissue, typically diseased tissue, from a target site, typically within a patient's breast, leaving access to the target site. An expandable element is introduced into and expanded within a void at the target site. A determination is made whether all of the target tissue at the target site was removed. This determination step may take place before or after the expandable element is introduced into the void. If it is determined that all of the target tissue was not removed, then a layer of tissue that at least partially surrounds the expanded element, and the expanded element itself, is removed from the patient. The removal of the layer of tissue and the expanded element may take place generally simultaneously. Using this procedure, the layer of tissue may be removed in a substantially intact form with improved geometric precision; this permits the physician, or other health care professional, to inspect the outer surface of the layer of tissue for evidence of the target tissue. Conventional techniques typically result in the removal of tissue fragments, which often makes it difficult or impossible to determine where the diseased tissue originated from, or in the removal of one or more excessively large sections of tissue. By maintaining the void using an expandable element and removing a layer of tissue at least partially surrounding the expandable element, the physician can make a much more geometrically precise and more accurate assessment of whether all of the target tissue has been removed than with conventional techniques while reducing the amount of additional tissue that needs to be removed.

Another aspect of the invention is also directed to an intraoperative tissue treatment method used following the removal of target tissue from a target site leaving a void at the target site. In this method the suction inlet of a section device is located so to be in fluid communication with the void at the target site; this may be carried out by positioning the suction inlet within the void. Fluid, typically including one or both of gas and liquid and potentially including particulates, is then withdrawn through the suction inlet so to at least partially collapse the tissue defining the void. A determination is then made whether all of the target tissue at the target site was removed. This determination may be made before or after the suction inlet is in position. If all of the target tissue has not been removed, at least a portion of the collapsed tissue is removed from the patient. This procedure may be carried out using a blocking element at a position distal of the target site. The blocking element may be removed during the removing step. The removing step may be carried out by passing a tissue separator through tissue surrounding the target site; the tissue separator may comprise a radially expandable, tubular mesh material. The removing step may be carried out by separating a layer of tissue from the surrounding tissue, maintaining the separated tissue layer in a substantially intact form, and then inspecting the outer surface of the separated layer of tissue for evidence of the target, typically diseased, tissue. This procedure also permits the physician to accurately determine whether all of the target tissue has been removed while reducing the amount of additional tissue that needs to be removed from the patient.

A further aspect of the invention is directed to an intraoperative tissue treatment method, for use following the removal of tissue from a target site leaving a void at the target site and a sheath along a passageway from a region external of the patient to the void at the target site. According to this method, the sheath is maintained at least part way, and preferably completely, along the passageway from the region external of the patient to the void at the target site. A flexible implant is passed through the sheath and into the void so to at least substantially fill the void with the implant. The implant may be a non-bioabsorbable bag-type implant. The sheath is then removed from the patient. According to this aspect of the invention the implant may be placed at the site of tissue removal soon after the removal of the tissue for both aesthetic and therapeutic reasons. That is, the implant may not only simply fill the void, but may carry agents such as temporary radioactivity agents, steroids and chemotherapeutic agents. The invention is based on the recognition that it would be desirable to insert an implant into a void while the sheath providing access to the void is still in place following the tissue removal procedure. Doing so reduces the number of times the target site needs to be surgically accessed to reduce tissue trauma, chance of infection and cost while aiding healing.

Other features and advantages of the invention will appear from the following description in which the preferred embodiments and methods have been set forth in detail in conjunction with the accompanying drawings.

BRIEF DESCRIPTION OF THE DRAWINGS

FIG. 7A illustrates a cross-sectional view of a patient's breast following removal of tissue at a target site, and illustrating a cavity created by the removed tissue, a sheath extending to the cavity, and an expandable element insertion device passing through the sheath into the cavity;

FIG. 7B illustrates an expanded expandable element within the void of FIG. 7A;

FIGS. 7C–7E illustrate a loop type cutter, shown in more detail in FIGS. 8A–8F, separating a layer of tissue surrounding the expanded element;

DESCRIPTION OF THE SPECIFIC EMBODIMENTS

Figure 1A:
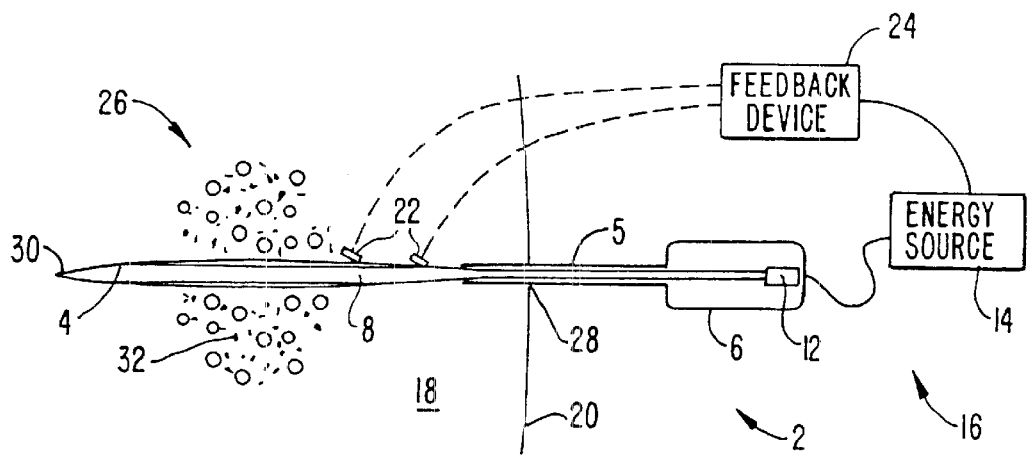
FIGS. 1A–1C illustrate the use of a tissue removal assembly made according to the invention.
Figure 1B:
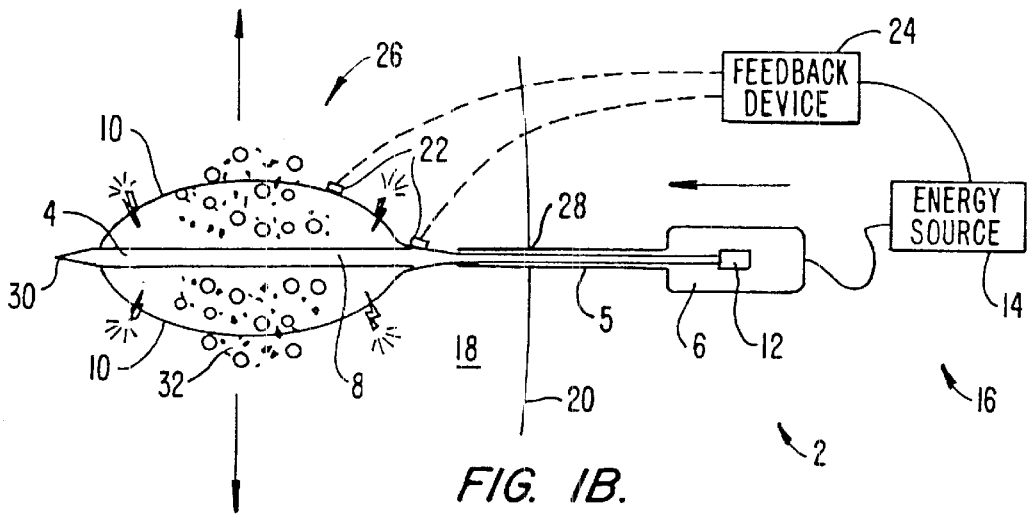
Figure 1C:
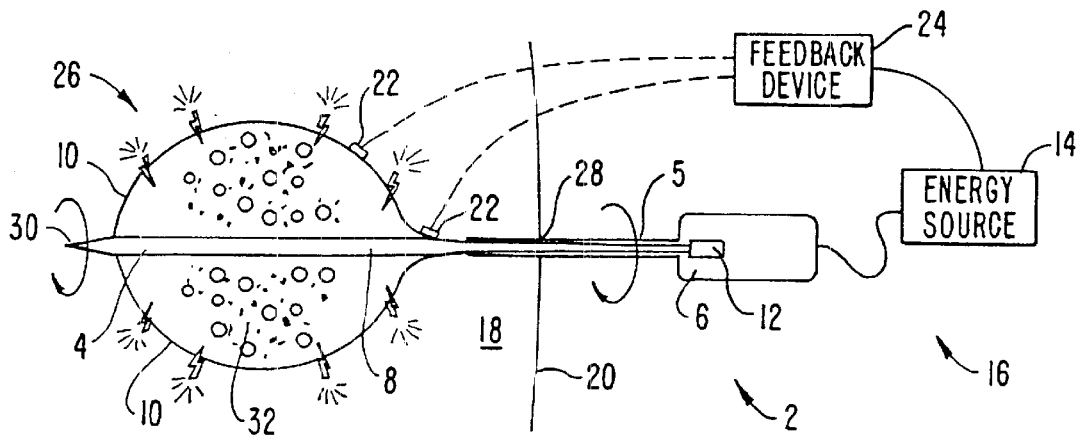

FIGS. 1A–1C illustrate the use of a tissue removal assembly 2. Tissue removal assembly 2 includes a support shaft 4 passing through an introducer sheath 5 extending from a handle 6. The distal portion 8 of shaft 4 has a pair of tissue separation wires 10 mounted thereto. Wires 10 are movable from a retracted state of FIG. 1A to a fully extended state of FIG. 1C by moving a slide 12 mounted to handle 6 as indicated in FIGS. 1A–1C. Wires 10 are typically made of tungsten or stainless steel and may have a round, rectangular or other cross-sectional shape depending upon the type of tissue and other matter expected to be encountered. U.S. patent application Ser. No. 09/248,088 and Provisional Applications No. 60/154,394 (filed Sep. 7, 1999 and entitled Oncological Apparatus and Method for Use) and No. 60/200,546 describe various tissue separation elements. Wires 10 are coupled to an energy source 14 to supply wires 10 with appropriate energy to aid the cutting or other separating actions of the wires, including electrical, RF, vibrational, electromagnetic, etc. Together, handle 6 and energy source 14 constitute a wire tissue separation element driver 16 because both act to help move wires 10 through tissue 18 beneath a skin surface 20 of the patient.

Appropriate sensors 22 are mounted to one or more of wires 10 and shaft 4. Sensors 22 could be portions of wires 10 themselves. Sensors 22 may include strain gauge sensors, pressure sensors, temperature sensors, etc. Sensors 22 are coupled to a feedback device 24 through sheath 5; feedback device 24 is connected to energy source 14 to ensure that energy source 14 provides an appropriate level of energy to wires 10.

Assembly 2 is used to percutaneously access a target site 26 through an access site 28 in skin surface 20 while in the retracted state. The tip 30 of shaft 4 is positioned distally of the target tissue mass 32. In some situations it may be desirable to pass tip 30 directly through target tissue mass 32 while in other situations it may be desirable to have shaft 4 pass to one side of target tissue mass 32 or proximal to the tissue mass as in FIGS. 7A–9D. Once properly positioned, which is preferably accomplished with the aid of remote visualization techniques, such as x-rays, ultrasound, etc., slide 12 is moved in a distal direction causing wires 10 to arc outwardly from the retracted state of FIG. 1A, through the intermediate extended state of FIG. 1B and to the fully extended state of FIG. 1C. Wires 10 are preferably energized, typically by heating using resistance or RF heating techniques, as wires 10 pass through tissue 18. This is very important when wires 10 pass through target tissue mass 32 and the target tissue mass contains, or possibly contains, cancerous or other diseased tissue. By appropriately energizing wires 10, the tissue wires 10 pass through is, for example, cauterized so that no viable diseased tissue is pulled along with the radially outwardly expanding wires; this helps to keep the healthy tissue surrounding target tissue mass 32 free from viable diseased tissue. In addition to heating or vaporizing the tissue, tissue removal assembly 2 may be provided with vibrational, reciprocating or other mechanical energy to help passage of wires 10 through tissue 18.

Once fully expanded, tissue removal assembly 2 is rotated, typically by the user manually grasping and rotating handle 6. If the desired, a motorized or other non-manual rotation of assembly 2 could be provided for. Sensors 22 provide appropriate information to feedback device 24 so to ensure a proper amount of energy is supplied to wires 10 to, among other things, ensure proper cauterization of the tissue as wires 10 are moved readily outwardly while not overly damaging the tissue. Therefore, if wires 10 cease to be driven and thus stop moving through the tissue, feedback can result in a halt in the supply of energy to wires 10. Once in the fully extended state of FIG. 1C, the amount of energy supplied to wires 10 may not need to be as great as when, for example, wires 10 pass through only healthy tissue.

In the embodiment of FIGS. 1A–1C two wires 10 are used. This causes target tissue mass 32 to be cut away from the surrounding tissue in two contiguous tissue masses. If desired, only a single wire 10 or more than two wires 10 could be used. The number of wires may be limited to, for example, 3 or 4 so that the sections removed are large enough to be identifiable. However, if one were to put additional wires into the assembly, even if only one wire was used for severing the tissue, the additional wires may help with removal of the tissue as they may be used to encapsulate the tissue. Using the method described with respect to FIGS. 1A–1C, the entire target tissue mass 32 may be removed in a simultaneous manner. This aspect of the invention will be described in more detail below with reference to FIGS. 4A–4D. All or part of the procedure, such as expanding, cutting, rotating, energizing, etc., could be automated.

Figure 2:
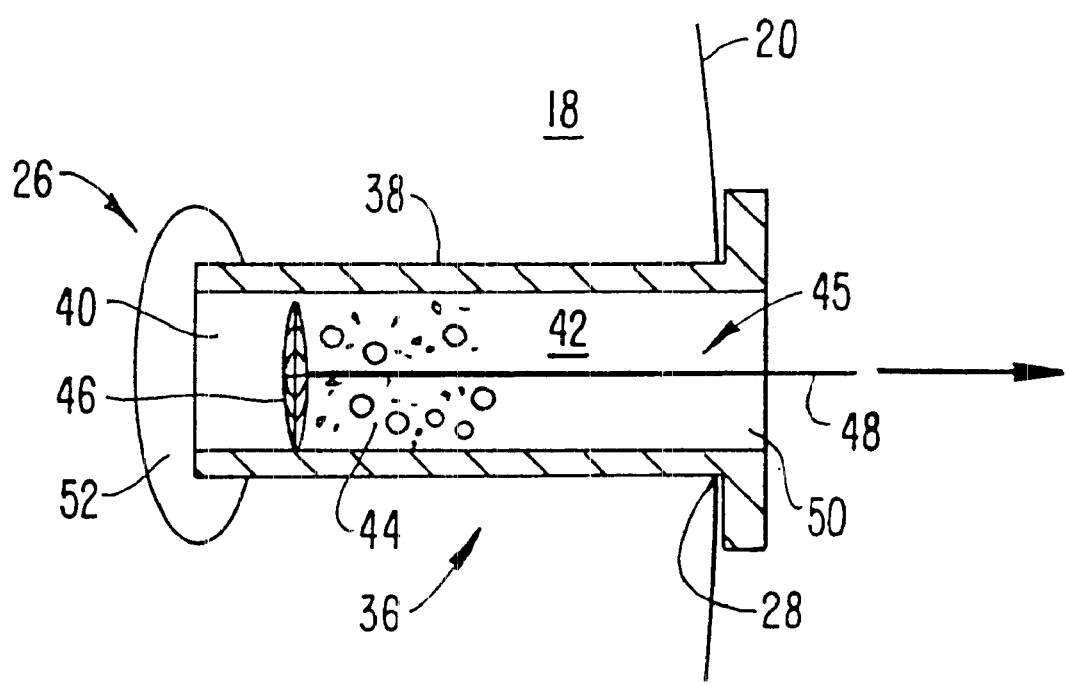
FIG. 2 shows the use of a sleeve which helps prevent seeding of a tissue tract and provides access to a void within the patient.

FIG. 2 illustrates a sleeve 36 used to help prevent seeding of a tissue tract 38 extending between access site 28 and target site 26. Protective sleeve 36 is positioned along tissue tract 38 and has a distal opening 40, preferably positioned adjacent to or within target site 26, and an open interior 42. Target tissue 44 is moved from target site 26 through opening 40 and into open interior 42. FIG. 2 illustrates this having been accomplished using a tissue engagement device 45 having a radially expandable mesh device 46 at the distal end of a shaft 48. Mesh device 46 is of a type which can be movable from a generally cylindrical orientation, not shown, to the radially extended configuration shown in FIG. 2 by pushing the distal ends of the cylindrical mesh material towards one another. Examples of this type of mesh structure can be found in U.S. patent application Ser. No. 09/376,678 filed Aug. 18, 1999, entitled Target Tissue Localization Device and Method and in Provisional Application No. 60/200,546. Other methods and devices for moving target tissue 44 from target site 26 into interior 42 can also be used. Alternatively, the end of sleeve 36 could be used to sever the tissue while sleeve 36 is moved forward and a cutting/separating snare, see FIGS. 8A–8F, could separate the distal side of the tissue. Target tissue 44 can then be removed from the patient by either leaving protective sleeve 36 in place and sliding the target tissue out through the opened proximal end 50 of sleeve 36 or by removing the entire structure, that is protective sleeve 36, mesh device 46, shaft 48 and target tissue 44 therewith, from tissue track 38 of the patient. Suction may also be used to remove tissue. Removed tissue may be analyzed to see if additional tissue needs to be removed.

Access to a void 52 within a patient can be maintained by placing sleeve 36 along tissue tract 38 and leaving it in place. This method may be accomplished after removal of, for example, a biopsy specimen or an entire suspect tissue mass. This provides convenient and accurate re-access to void 52. Such re-access may be used, for example, when additional tissue samples are needed, therapeutic agents (including heat treatment agents, mechanical treatment agents, chemical agents and radioactive agents) need to be delivered to void 52, a prosthesis is to be implanted into void 52, or for other reasons. See the discussion below with reference to FIGS. 10A–10C.

Figure 3A:
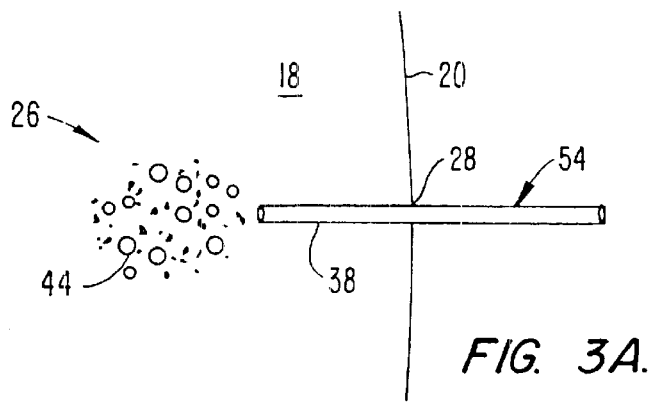
FIGS. 3A–3H illustrate a further aspect of the invention by which percutaneous removal of target tissue from a target site within the patient is accomplished using a radially expandable/collapsible tubular shaft.
Figure 3B:
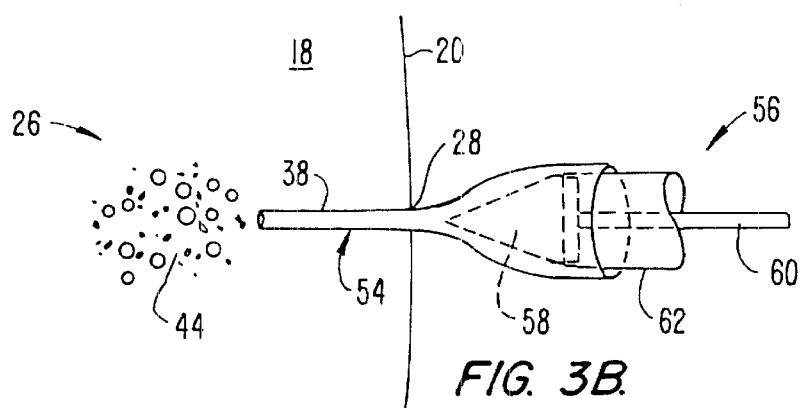
Figure 3C:
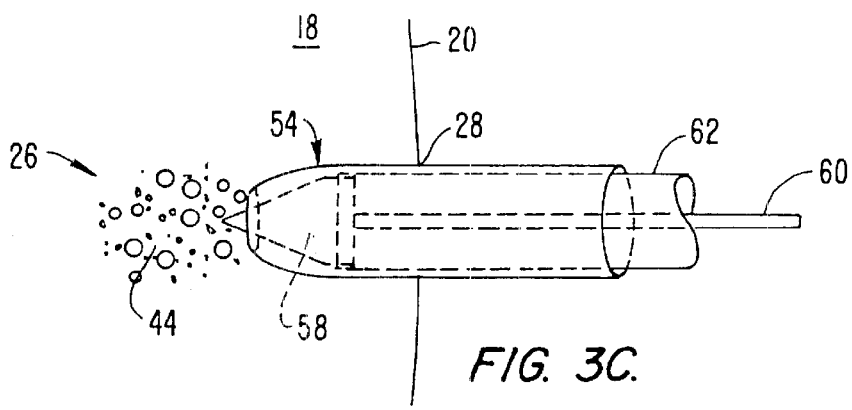
Figure 3D:
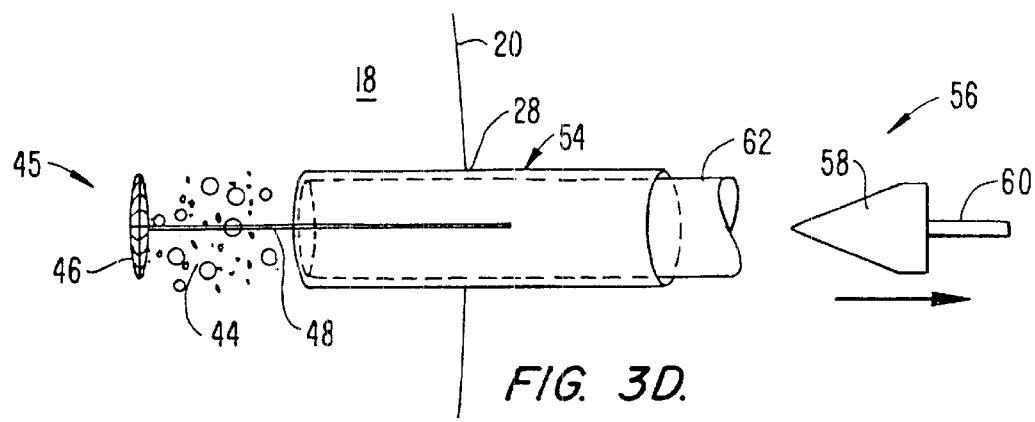
Figure 3E:
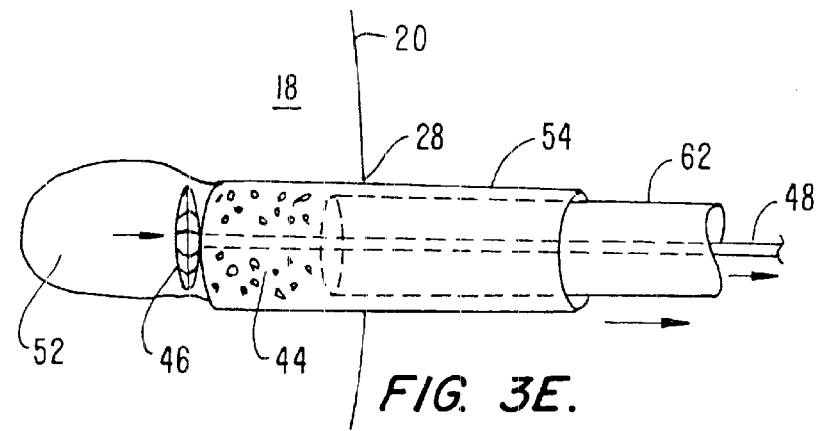

FIGS. 3A–3H illustrate the percutaneous removal of target tissue 44 from target site 26. A hollow, radially expandable/collapsible tubular shaft 54 is passed along tissue tract 38 when in a radially collapsed condition as shown in FIG. 3A. FIG. 3B illustrates the introduction of a tubular enlarger 56 including a conical tip 58 mounted to the distal end of a shaft 60 and a stabilizing sleeve 62 extending proximally from conical tip 58. As illustrated in FIGS. 3B and 3C, pushing enlarger 56 through shaft 54 causes the shaft to radially enlarge along its length; stabilizing sleeve 62 resists the tendency of shaft 54 to radially collapse. Once sleeve 62 is properly positioned within shaft 54, shaft 60 and tip 58 therewith are removed from within sleeve 62 as shown in FIG. 3D. Also, FIG. 3D illustrates the positioning of a tissue engagement device 45 to help draw a sample of target tissue 44 into the interior 64 of sleeve 62 as suggested in FIGS. 3D and 3E.

Figure 3F:
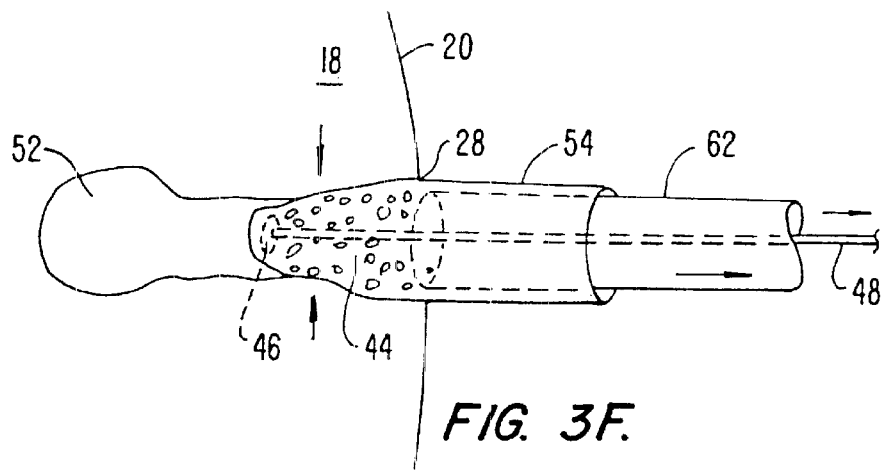
Figure 3G:
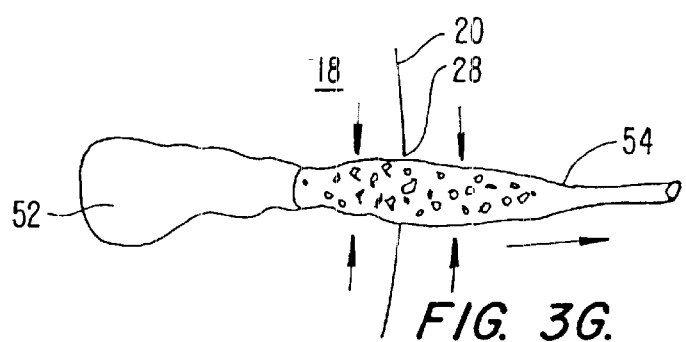
Figure 3H:
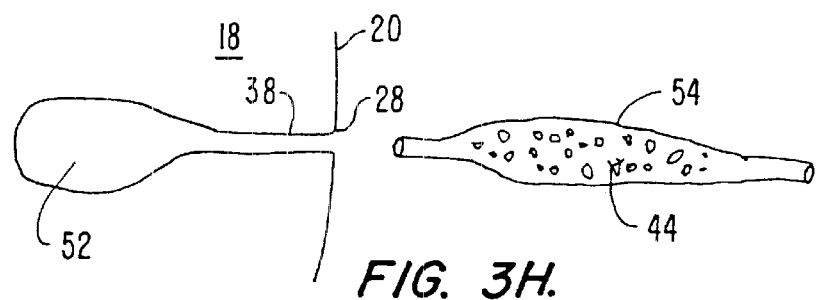

At this point a sample of the target tissue 44 may be removed from the patient by simultaneously removing shaft 54 in its enlarge diameter form, sleeve 62 and device 45 as a unit. Alternatively, stabilizing sleeve 62 may be removed as device 45 pulls tissue 44 into shaft 54 while shaft 54 remains in place. This suggested in FIGS. 3E and 3F and permits shaft 54 to return towards its initial, radially contracted condition thus causing the tissue sample housed therein to be radially compressed. The collected target tissue 44 remains within shaft 54 when sleeve 62 is removed from shaft 54 and mesh device 46 is collapsed (see FIG. 3F). Shaft 54 then naturally assumes a smaller diameter condition as shown in FIGS. 3F and 3G which permits shaft 54 and the target tissue therein to be removed through access site 28 as shown in FIGS. 3G and 3H. In this way the size of access site 28 may be smaller than the original size of target tissue 44. Device 45 may remain within shaft 54 during this removal from the patient, or device 45 may, as suggested in FIGS. 3G and 3H, be removed from shaft 54 along with sleeve 62. Alternatively, mesh device 46 may not be required as mentioned above.

The entire shaft 54 was enlarged in the embodiment of FIGS. 3A–3H. If desired, only the part of shaft 54 within the patient may need to be expanded. This would reduce the maximum size which access site 28 is forced to assume, even if only temporarily. The following U.S. Patents show radially-expanding dilators: U.S. Pat. Nos. 5,183,464; 5,431,676; 5,454,790.

Figure 4A:
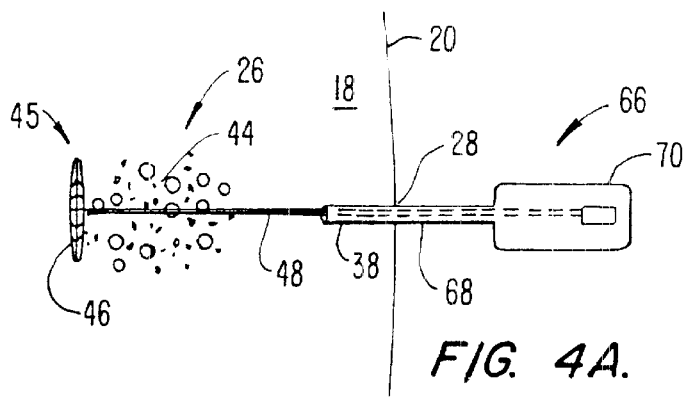
FIGS. 4A–4D show a method for percutaneously removing an entire tissue mass from a target site.
Figure 4B:
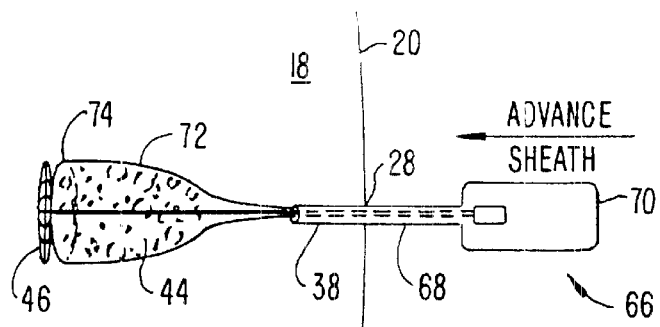
Figure 4C:
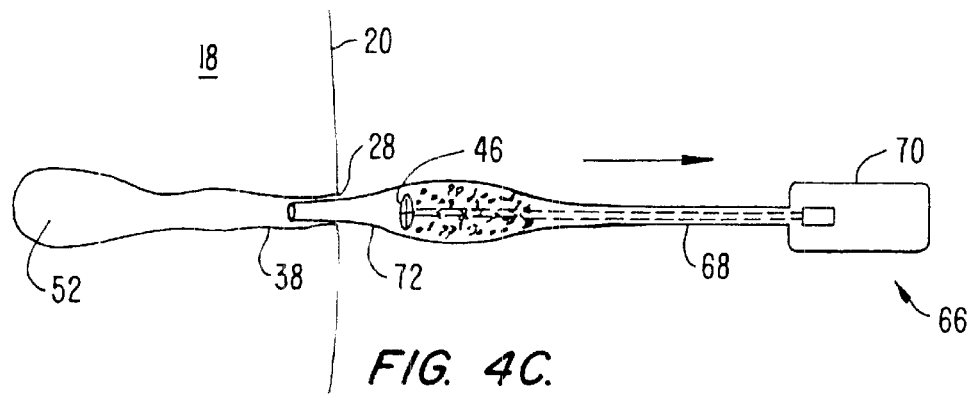
Figure 4D:
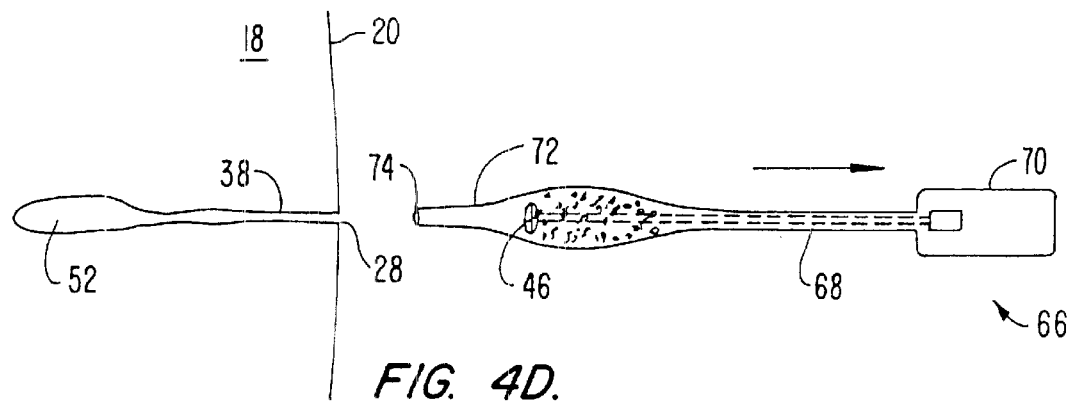

FIGS. 4A–D illustrate a method for percutaneously removing an entire tissue mass containing target tissue 44. A tissue removal assembly 66 includes a sheath 68 extending from a proximal end adapter 70 and passes through an access site 28 and along tissue tract 38. Sheath 68 houses a tissue engagement device 45, shown in FIG. 4A, after having passed by or through target tissue 44 and manipulated to cause mesh device 46 to assume a radially expanded condition. Next, a tubular mesh device 72, or other suitable mechanism, is used to surround target tissue 44. Device 72 is of the type in which a tubular mesh material having an open distal end expands radially outwardly as it is compressed axially. That is, the resistance to the axial movement mesh device 72 causes it to contract axially and expand radially to assume the generally funnel-shaped configuration of FIG. 4B. As shown in FIG. 4B, mesh device 46 acts as a blocking element and mesh device 72 acts as a removing element. Together devices 46, 72 at least substantially surround, and preferably fully surround or envelope, target tissue 44.

The entire suspect tissue mass, that is the mass including target tissue 44 and an amount of surrounding tissue(or only a portion of target tissue 44, such as for biopsy), can be removed through access site 28. To help prevent trauma to access site 28 during such removal, mesh device 46 and tubular mesh device 72 are caused to contract radially, thus compressing target tissue 44 into a smaller diameter mass for ease of removal from the patient. This is suggested in FIGS. 4C and 4D. The construction and use of structure similar to device 72 is described in patent application Ser. No. 09/248,008 and Provisional Application No. 60/200,546. Note that the structure shown in FIGS. 1A–1C could be used to severe target issue 44 so that the entire suspect tissue mass (or a part of the suspect tissue mass, such as for biopsy), that is including target tissue 44, may be simultaneously removed as two contiguous pieces from the patient along the tissue tract. It is expected that the entire suspect tissue mass could be severed into at most four contiguous pieces and still be simultaneously removed in a useful condition for further testing and/or evaluation. One such structure could use the cutting device of FIGS. 1A–1C plus a mesh material similar to tubular mesh device 72 which could be guided by expanded wires 10 to surround the suspect tissue mass. As seen by comparing FIGS. 4B and 4C, the largest lateral dimension of the access opening 28 is smaller than the largest lateral dimension of a suspect tissue mass prior to removal; radially or laterally squeezing the suspect tissue mass permits removal of the tissue mass with minimal trauma to the patient. The suspect tissue mass may be monitored for disease prior to, during and/or after removal from the patient.

Figure 5A:
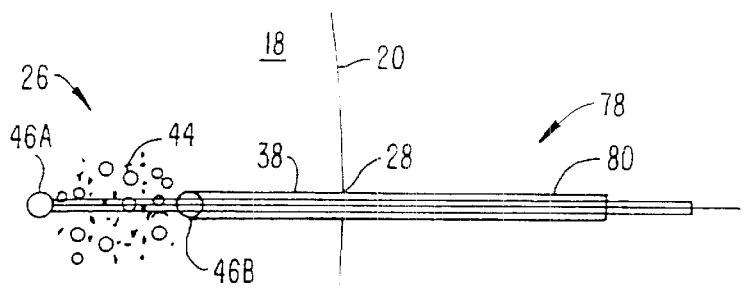
FIGS. 5A–5D illustrate a target tissue removing device including a pair of tissue engaging devices which bracket the target tissue.
Figure 5B:
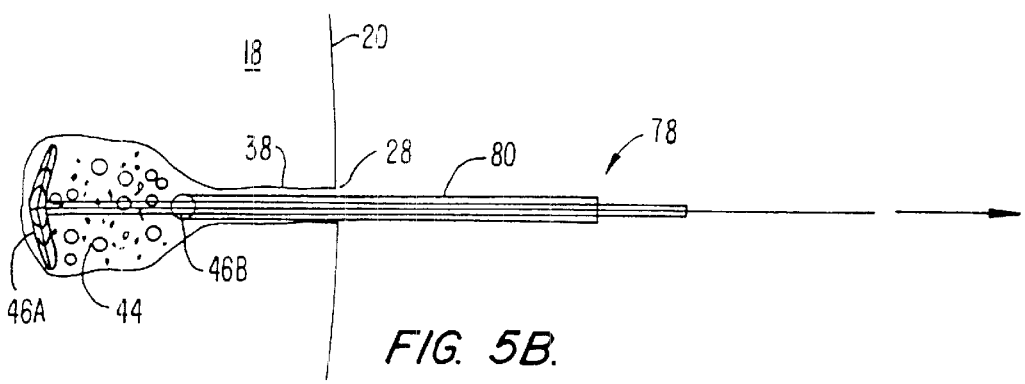
Figure 5C:
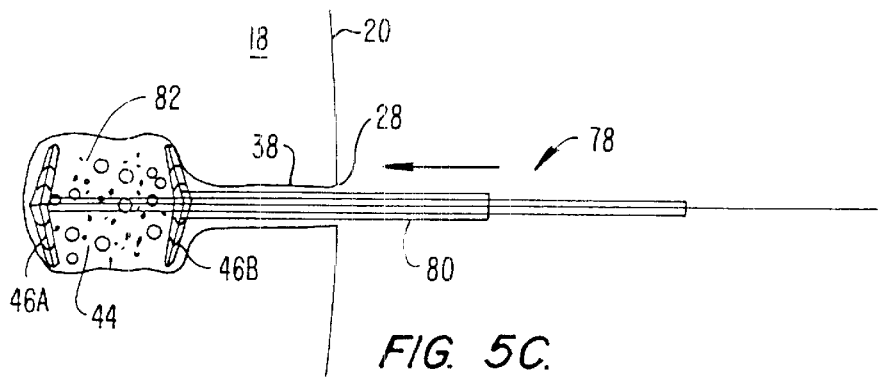
Figure 5D:
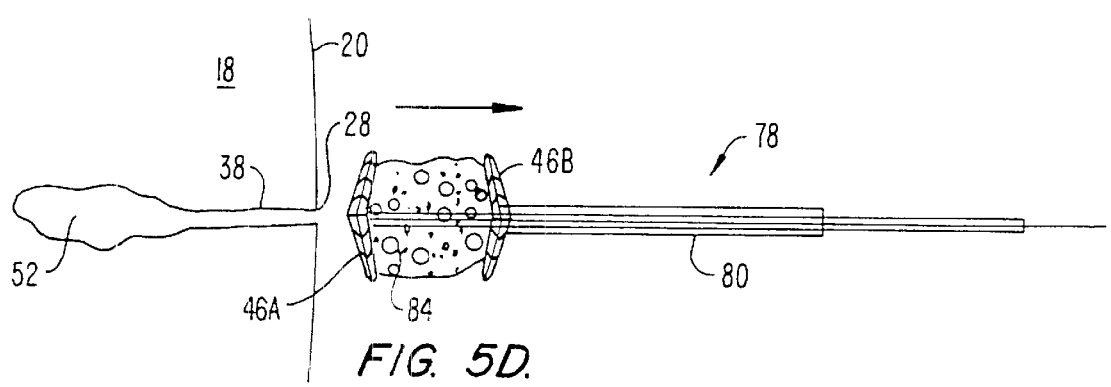

FIGS. 5A–5D illustrate a target material removing device 78 including a sheath 80 within which a pair of tissue engaging devices 45 slidable pass. FIG. 5A illustrates device 78 passing through access site 28, along tissue tract 38 and to target tissue 44 at target site 26. The first and second mesh devices 46A, 46B are placed at distal and proximal locations relative to target tissue 44. Once in position, mesh devices 46 are expanded as shown in FIGS. 5B and 5C so to bracket target tissue 44. Mesh devices 46A, 46B in their expanded conditions are sized so to define a bracketed region 82 therebetween. Bracketed region 82 is preferably sized to completely contain the tissue mass including target tissue 44. When so bracketed, the health professional can locate target tissue 44 by virtue of the expanded mesh devices 46. In one embodiment mesh devices 46A, 46B are harder than the surrounding tissue so that target tissue 44 within bracketed region 82 may be found by palpation. In addition, expanded meshed devices 46A, 46B guide a surgeon in locating and excising the entire target mass using surgical techniques. The using of bracketing guides 46A, 46B is important because target tissue 44 is often difficult to differentiate from surrounding tissue both in appearance and in feel. After the surgeon has accessed target tissue 44, guided by bracketing mesh devices 46, the entire suspect tissue mass 84 can be removed as a single mass as suggested in FIG. 5D. It is expected that the device of FIGS. 5A–5D may be useful in both percutaneous and open incisional situations. Note that bracketing mesh devices 46A and 46B may be designed so that they are shaped like cones or funnels so that their opposed edges meet to sever and capture suspect tissue mass 84 therebetween.

Figure 6A:
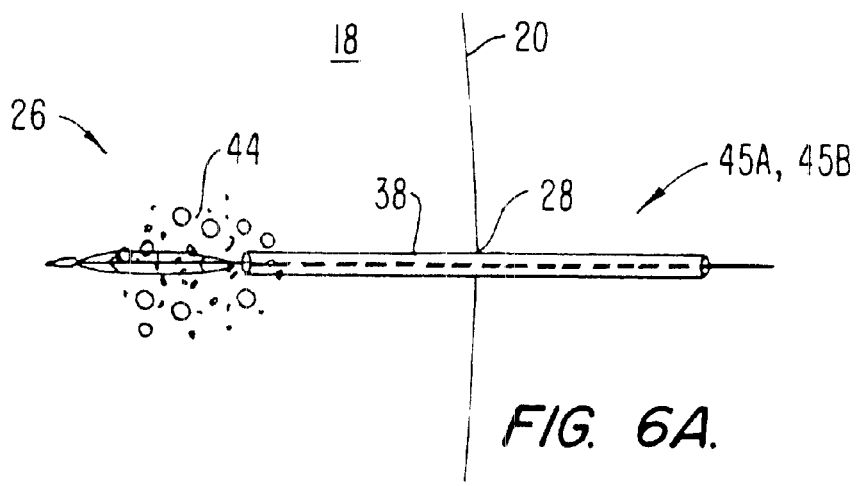
FIGS. 6A–6C show the use of a pair of locational elements, one of which is left in place after target tissue is removed to provide guidance for re-access to the target site.
Figure 6B:
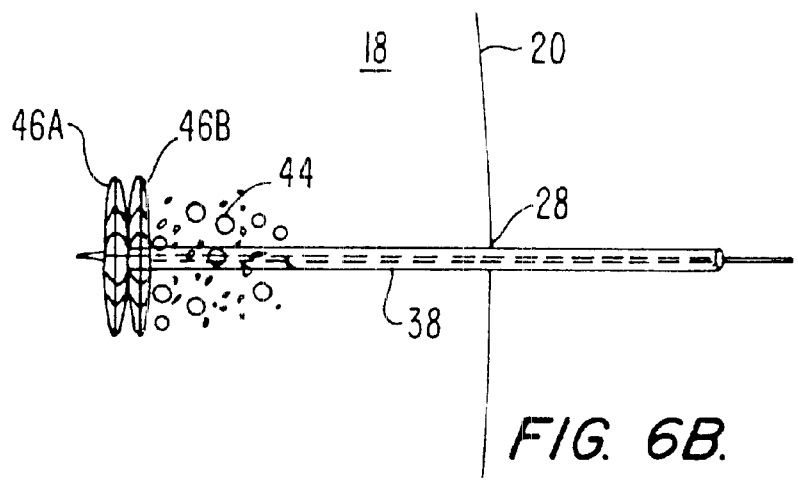
Figure 6C:
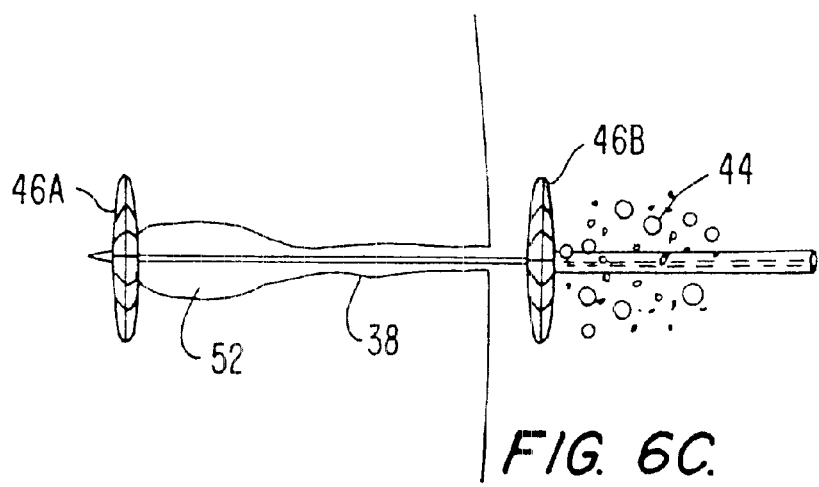

FIGS. 6A–6C show the use of essentially the same type of structure as in FIGS. 5A–5D but for a different purpose. In this case devices 45 are used as locational elements. In the preferred embodiment both of the locational elements have radially expandable elements, such as mesh devices 46, both of which are positioned distally of target tissue 44. After removal of target tissue 44, which may occur along with proximal device 45B, device 45A remains in place adjacent to the excisional site or void 52 created by the removal of target tissue 44. This may be used to help maintain void 52 open to aid re-access to the site. Maintaining void 52 open also permits insertion of a space-saving device or structure into void 52. Instead of using two radially expandable elements as portions of the locational devices, locational device 45A could be simply, for example, a catheter shaft in which with the distal end would remain at the distal end of excisional site 52.

Turning now to FIGS. 7A–12C, with like reference numerals referring to like elements, further aspects of the invention, relating to intraoperative tissue treatment methods, will be discussed. The treatment methods are designed to be intraoperative, that is practiced closely following the removal of target tissue from a target site, typically within a patient's breast, leaving access to the target site, such as introducer sheath 5 being left along tissue tract 38.

FIG. 7A illustrates a void 90 at target site 26 being accessed by an expandable element insertion device 92 through sheath 5. FIG. 7B shows an expanded balloon 94 at the distal end of insertion device 92 in an expanded condition substantially filling void 90. Balloon 94, or some other expandable element such as an expandable malecot 96 (FIG. 7J) or an expandable braided element 98 (FIG. 7K) may be expanded to a size greater that of void 90 thus expanding the void slightly. It may be desired to do this to compress the surrounding tissue to facilitate subsequent removal of a layer of tissue 100 from surrounding the expandable element 94 or for other reasons. The tissue that creates void 90 is tested to determine if all the target tissue, typically diseased tissue, has been removed. If it is determined that all of the target tissue has been removed, then the patient is closed in the usual fashion. However, there may be a need for access for additional or adjunctive therapy. Even further, another material or an implant may be placed inside the cavity prior to closing the cavity. Note that the step of determining whether all the target tissue has been removed may be accomplished before or after expandable element 94 has been positioned within void 90.

Figure 7F:
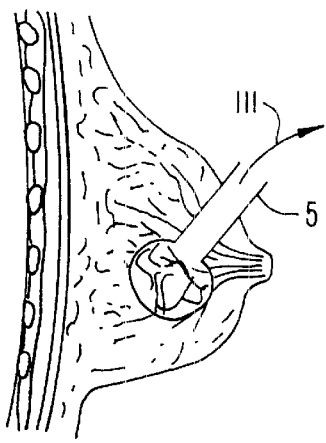
FIG. 7F illustrates the removal of the separated layer of tissue with the aid of suction.
Figure 7G:
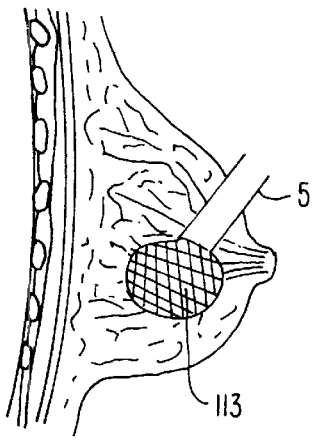
FIG. 7G illustrates an alternative to the use of suction in FIG. 7F using a radially expandable and contractible mesh material.

FIGS. 7C–7H show one method of separating tissue layer 100 from the surrounding tissue 18 by passage of a loop separator 102, shown also in FIGS. 8A–8F, over insertion device 92 and through sheath 5. Loop separator 102 includes a sheath 104 through which a cutter wire 106 passes. A loop 108 of wire 106 extends from the distal end 110 of sheath 104. As the distal end 110 of sheath 104 is moved distally, wire 106 is manipulated so that loop 108 first gets larger in size and then gets smaller in size as the loop passes around expanded balloon 94 thus separating tissue layer 100 from the surrounding tissue 18. To aid the cutting action of loop 108, the loop may, for example, have sharpened or roughened edges or the loop may be energized, such as by heating, or be supplied with mechanical vibrational or oscillatory energy. Other methods for separating tissue layer 100 may include, for example, the use of radially expandable and rotatable cutter wires as illustrated in FIGS. 1A–1C, the use of a mesh cutter as is discussed below with reference to FIGS. 9A–9D, or the use of tissue separation structure as is illustrated in FIGS. 11A–11H. After separating tissue layer 100 from the surrounding tissue 18, loop separator 102 may be removed for the subsequent removal of tissue layer 100 surrounding expanded element 94. FIG. 7F proposes the removal of tissue there 100 and expanded element 94 through introducer sheath 5 by the use of suction as indicated by arrow 111. FIG. 7G suggests the use of a mesh type capturing mechanism 113 to envelop tissue layer 100 for removal from the patient. Capturing mechanism 113 may be similar to the tubular mesh material 112 discussed below with regard to FIGS. 9A–9D. Other types of capturing mechanisms may be used as well. In addition, loop separator 102 may be left in place and removed with tissue layer 100 during an appropriate procedure.

Figure 7H:
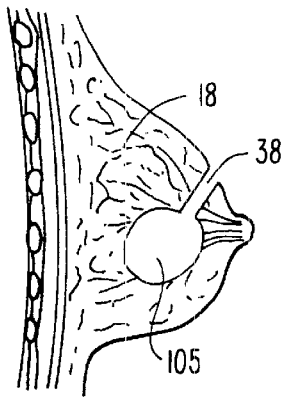
FIG. 7H illustrates the resulting cavity.
Figure 7I:
FIG. 7I illustrates an enlarged, simplified cross-sectional view of the layer of tissue removed during the steps of the FIGS. 7A–7H.
Figure 7J:
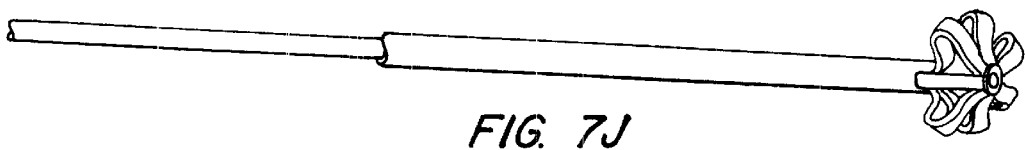
FIGS. 7J and 7K illustrate alternatives to the balloon-type expandable element of FIG. 7B.
Figure 7K:
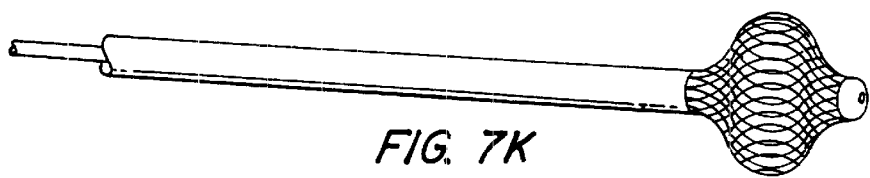
Figure 8A:
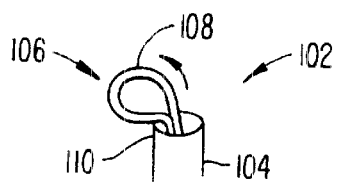
FIGS. 8A–8F illustrate the opening and closing movements of the loop type cutter shown in FIGS. 7C–7E.
Figure 8B:
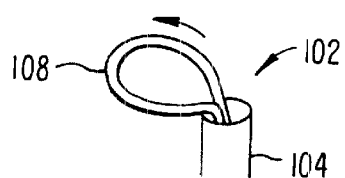
Figure 8C:
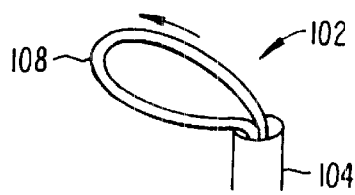
Figure 8D:
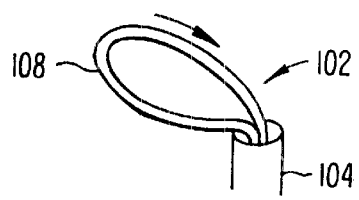
Figure 8E:
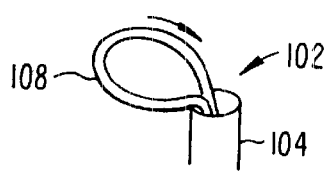
Figure 8F:
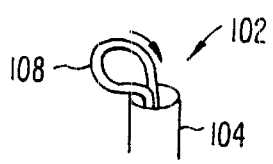

FIG. 7I illustrates, in simplified form, a cross-sectional view of tissue layer 100 removed from the patient. Tissue layer 100 comprises an inner, void-defining surface 101 and an outer surface 103. Outer surface 103 may be tested to check for the presence of target tissue so to determine if all the target tissue has been removed. If outer surface 103 tests positive for the presence of diseased tissue, a determination must be made as to how to deal with the diseased tissue remaining within the patient and surrounding the enlarged void 105 shown in FIG. 7K. One procedure may be to repeat the procedure using an enlarged expandable element 94 sized to fit within enlarged void 105. Other surgical or non-surgical techniques may be used as well. If it is determined that all of the target tissue has been removed, then the patient is closed in the usual fashion. However, there may be a need for access for additional or adjunctive therapy. Even further, another material or an implant may be placed inside the cavity prior to closing the cavity.

Figure 9A:
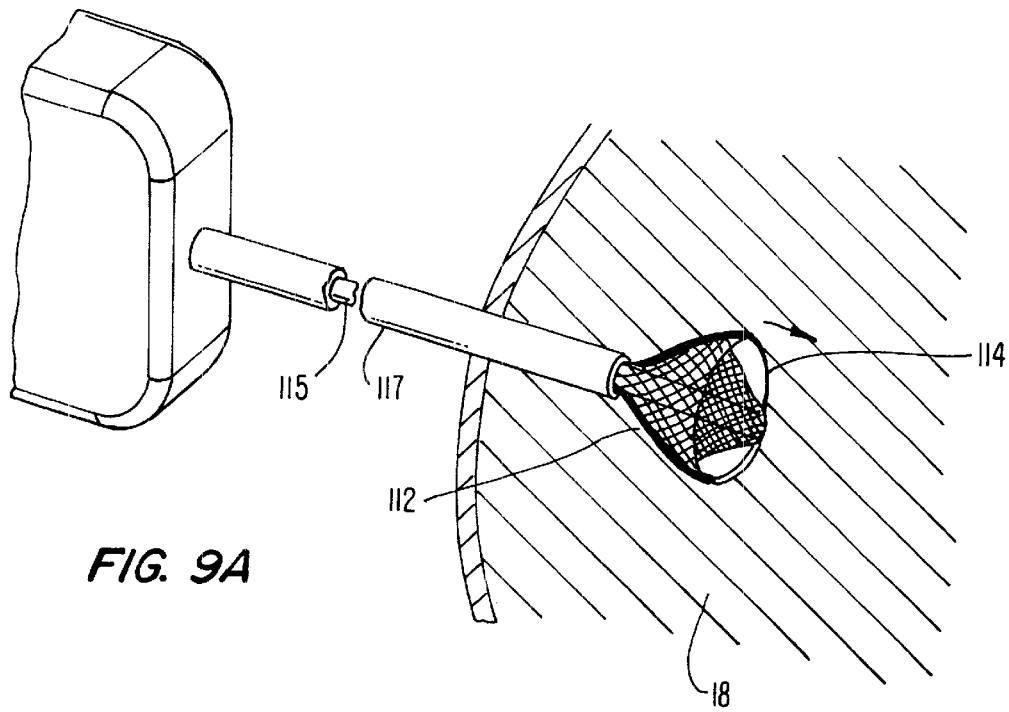
FIGS. 9A–9D illustrate the use of a radially expandable mesh type cutter to separate a layer of tissue surrounding a void having an expanded expandable element therein.
Figure 9B:
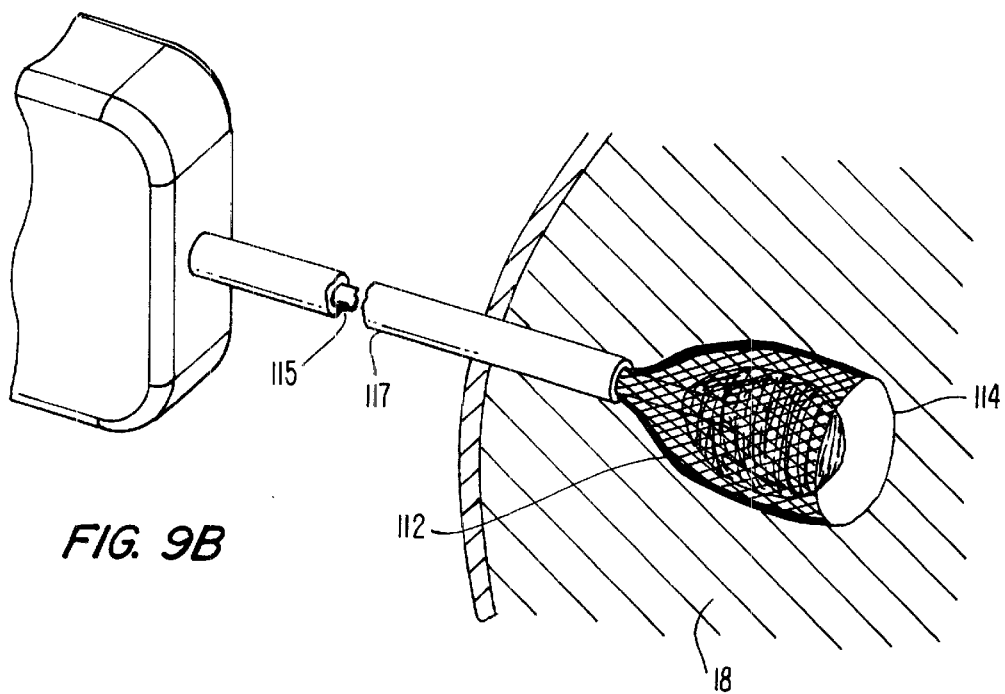
Figure 9C:
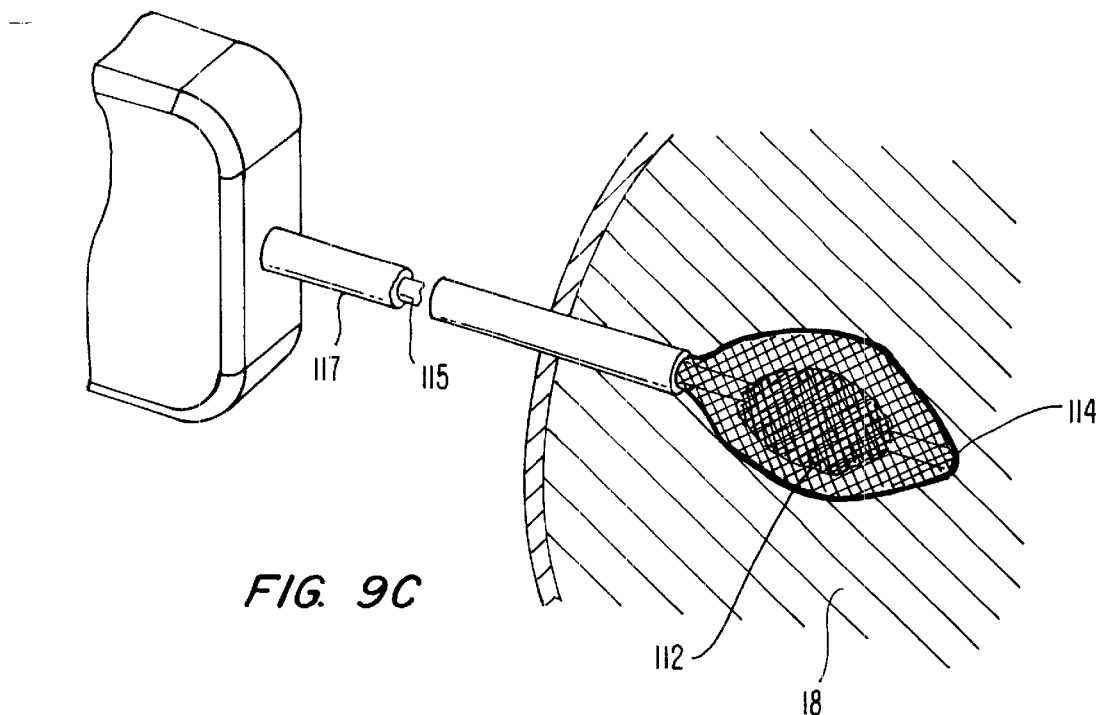
Figure 9D:
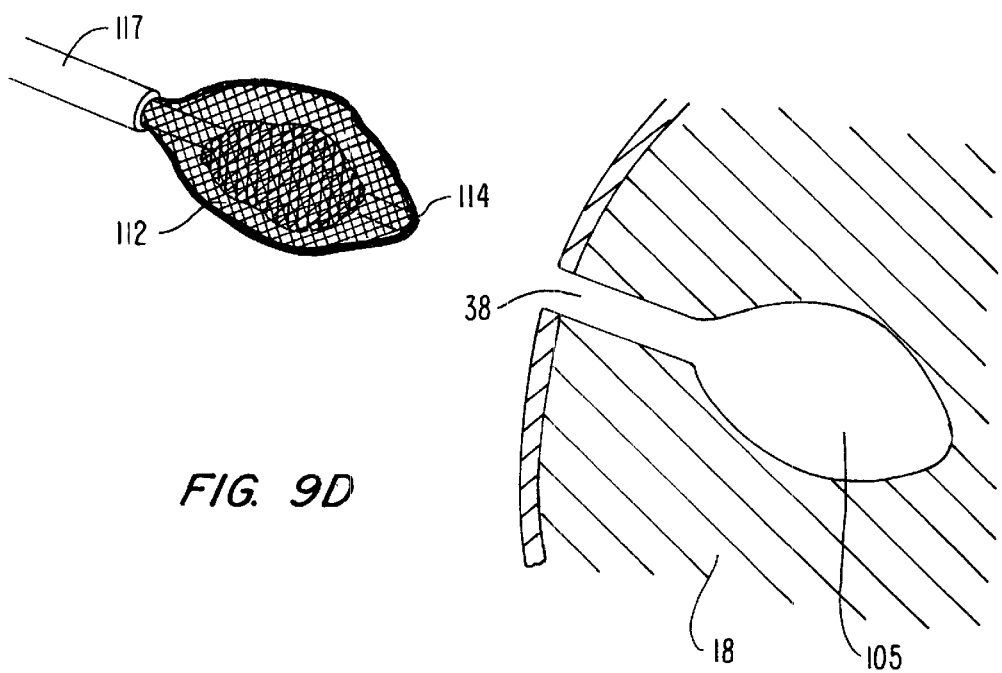

FIG. 9A illustrates the situation shown in FIG. 7B, that is with expandable element 94 expanded at target site 26, with the use of a tubular, radially expandable mesh cutter 112 to separate tissue layer 100 from surrounding tissue 18. Mesh cutter 112 is typically made of an electrically conducting metal or other material that will sever the tissue mechanically. Mesh cutter 112 is constructed so that when placed in compression, the distal, cutting edge 114 tends to radially expand. This is suggested in FIG. 9A. The amount and rate of radial expansion of cutting edge 114 may be controlled by, for example, the use of a pull wire or loop along the cutting edge. As cutter 112 continues to move distally from between inner and outer tubes 115, 117, distal cutting edge 114 is gradually pulled down to the closed condition of FIG. 9C so that mesh cutter 112 completely envelops tissue layer 100 to permit tissue layer 100, together with expandable element 94 therein, to be withdrawn simultaneously with mesh cutter 112 as suggested in FIG. 9D. This procedure helps to ensure tissue layer 100 is substantially intact for examination by the physician or other health-care professional.

Figure 10A:
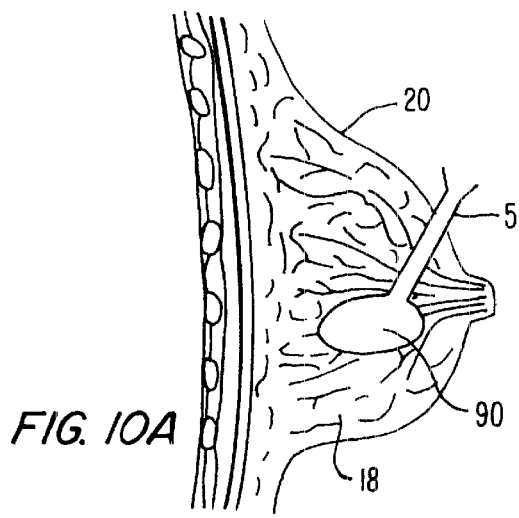
FIGS. 10A–C show the insertion of a flexible implant through a sheath providing access to a void within a patient's breast.
Figure 10B:
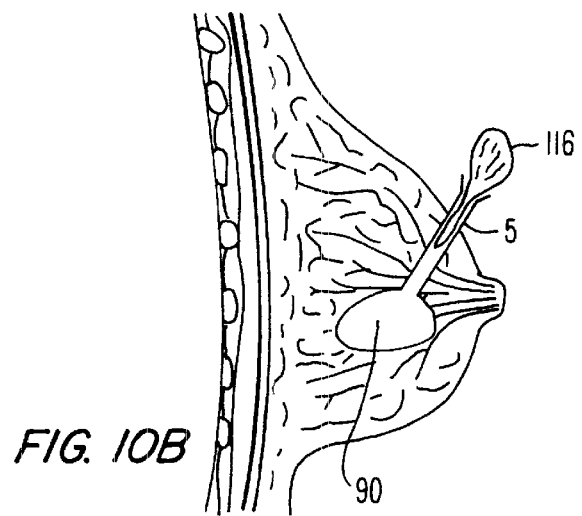
Figure 10C:
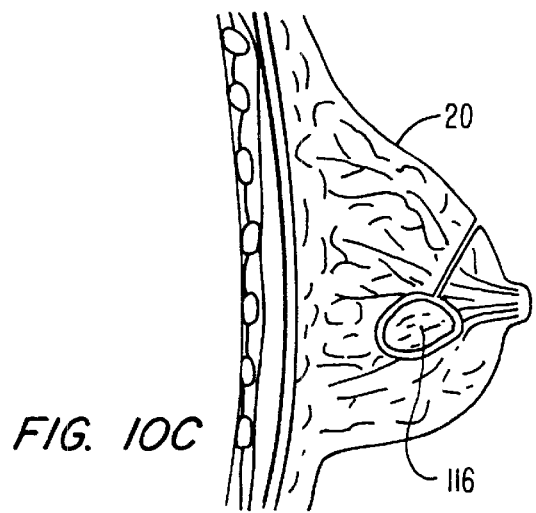

Another intraoperative treatment method, which may advantageously take place following the removal of target tissue from a target site leaving access, typically using sheath 5, to void 90 at the target site, relates to placing a flexible implant 116 into the void through the sheath. FIGS. 10A–10C illustrate the placement of a bag-type flexible implant 116, made of non-bioabsorbable material, through sheath 5 and into void 90 to at least substantially filling void. Implant 116 may also be a bioabsorbable material, such as collagen or a gel, that is eventually replaced with tissue. After flexible implant 116 is in place, sheath 5 may be removed as suggested in FIG. 10C. By maintaining sheath 5 in place after removal of tissue from the target site, the implant placement takes place in an efficient manner without the additional trauma and expense that would result if placed postoperatively. Other types of flexible implants, such as an implant that may be inflated once in place within the void, could be used. The flexible implant will typically be filled with a flowable, or at least a formable, material, such as a liquid, a gel, a granular material, or a combination thereof. Implant 116 preferably substantially fills void 90, that is fills at least about 60 percent of void 90, and may be sized to completely fill void 90 or to overfill, and thus enlarge, void 90, such as by about 20 percent or more.

Figure 11A:
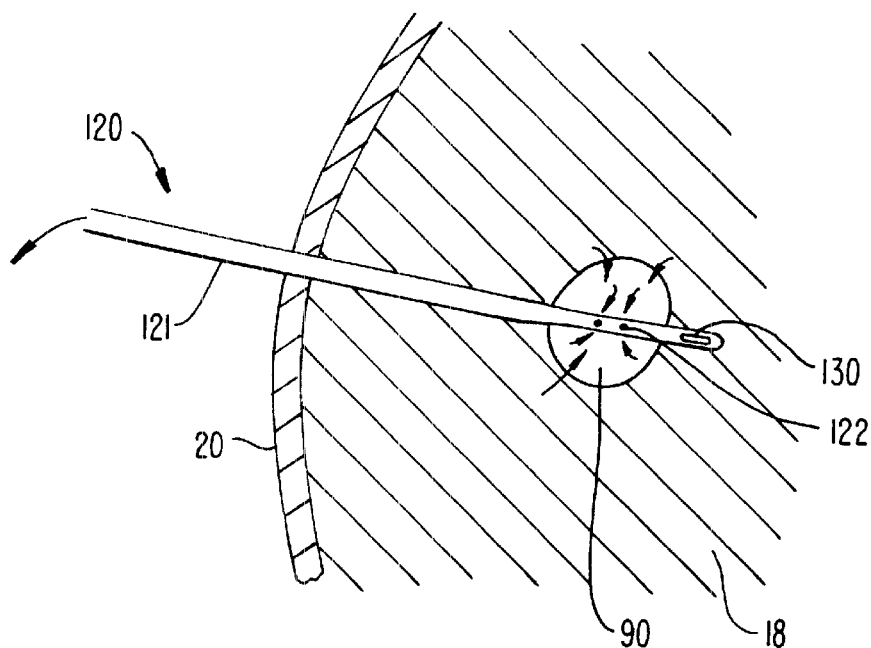
FIG. 11A illustrates placement of the suction inlet of a section device within a void at a target site within a patient.
Figure 11B:
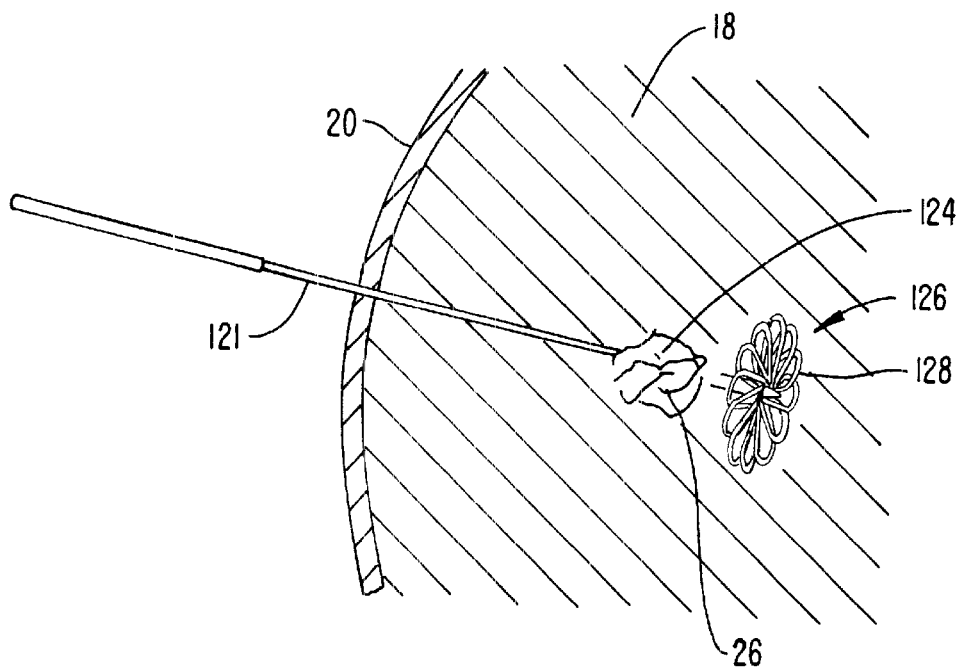
FIG. 11B shows a blocking element shaft passing through the collapsed tissue at the target site, created by withdrawal of fluid through the suction device of FIG. 11A, and a radially expanded blocking element positioned distally of the target site.
Figure 11C:
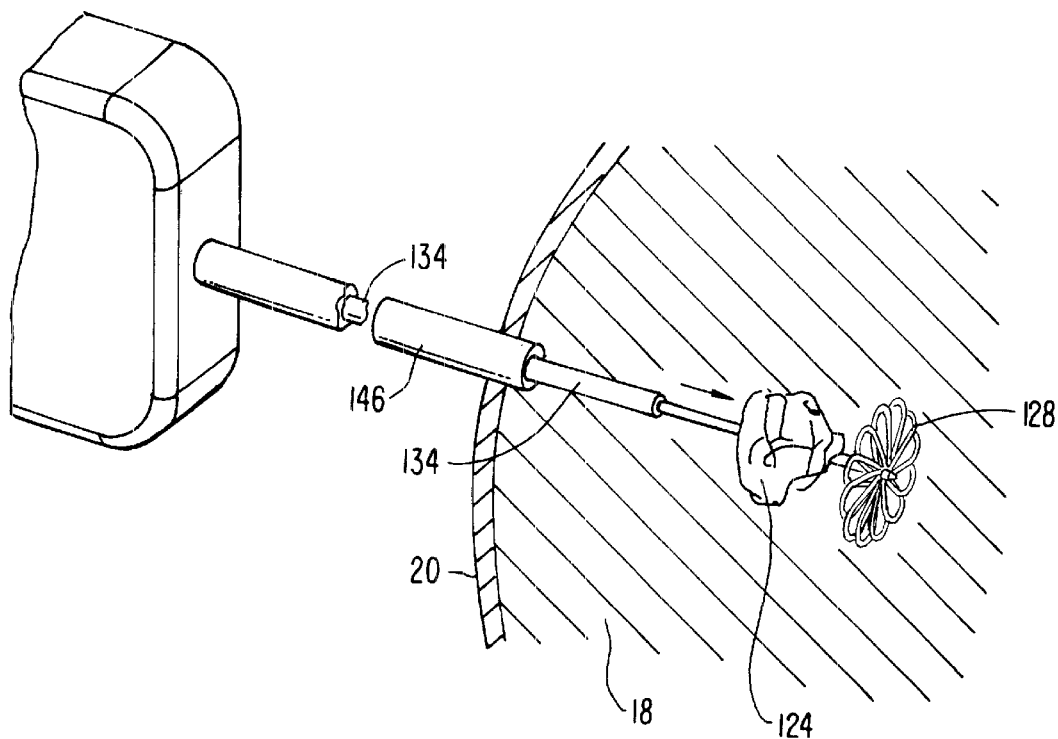
FIGS. 11C–11E illustrate the positioning of a wire tissue cutter at the collapsed tissue of FIG. 11B, the radial expansion of the wire tissue cutter and the rotation of the wire tissue cutter to separate a layer of tissue surrounding the target site.
Figure 11D:
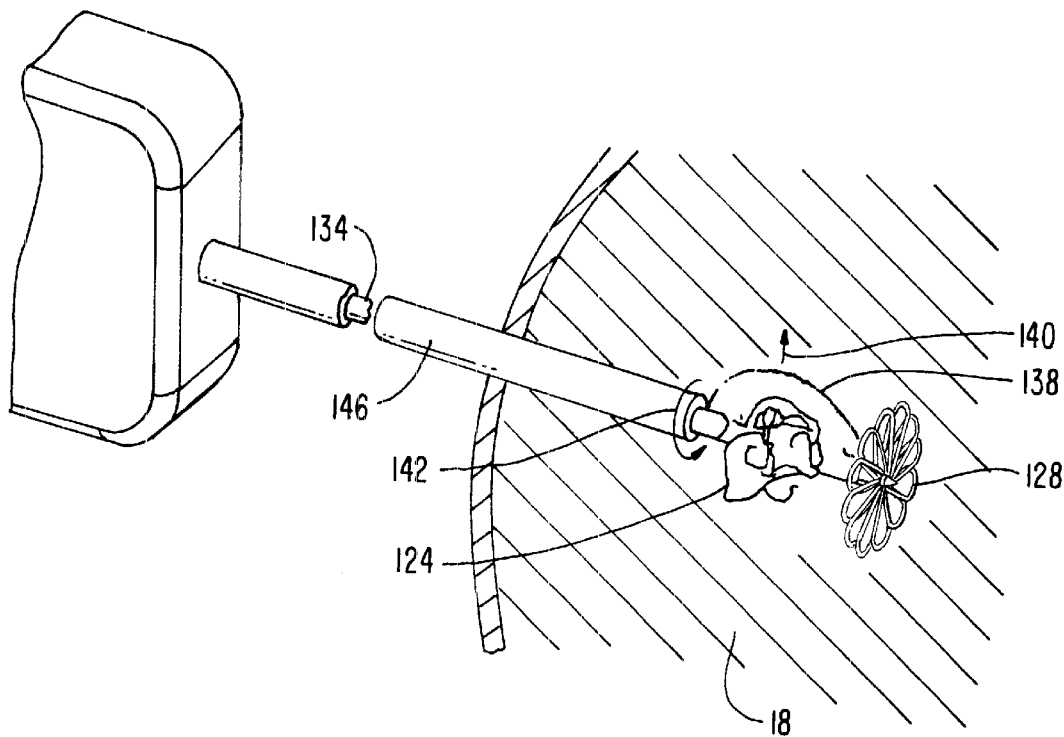
Figure 11E:
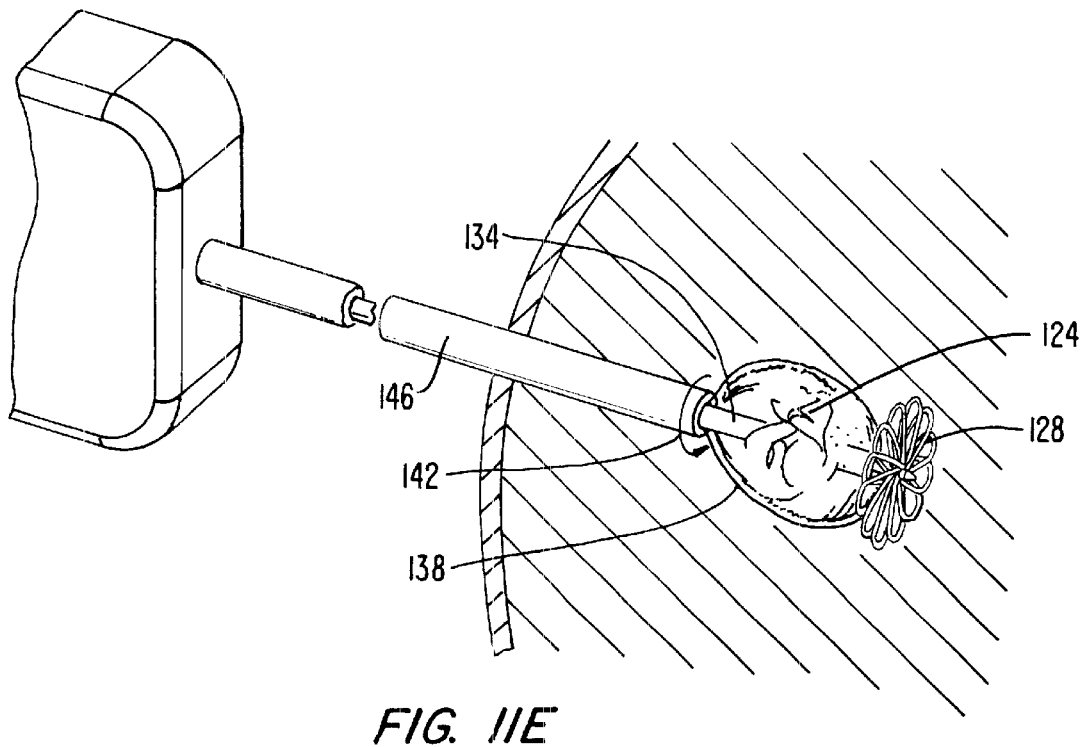
Figure 11F:
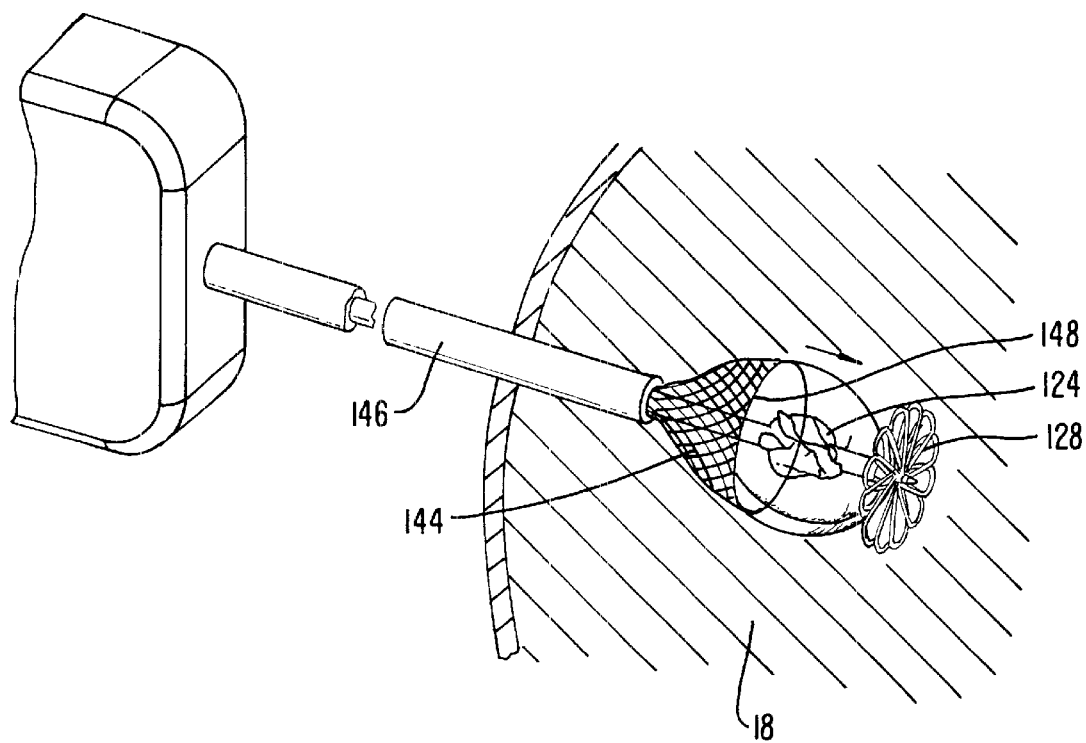
FIGS. 11F–11H illustrate passing a radially expandable, tubular mesh material between the separated layer of tissue and the surrounding tissue and then removal of the separated layer of tissue simultaneously with the removal of the tubular mesh material and the blocking element.
Figure 11G:
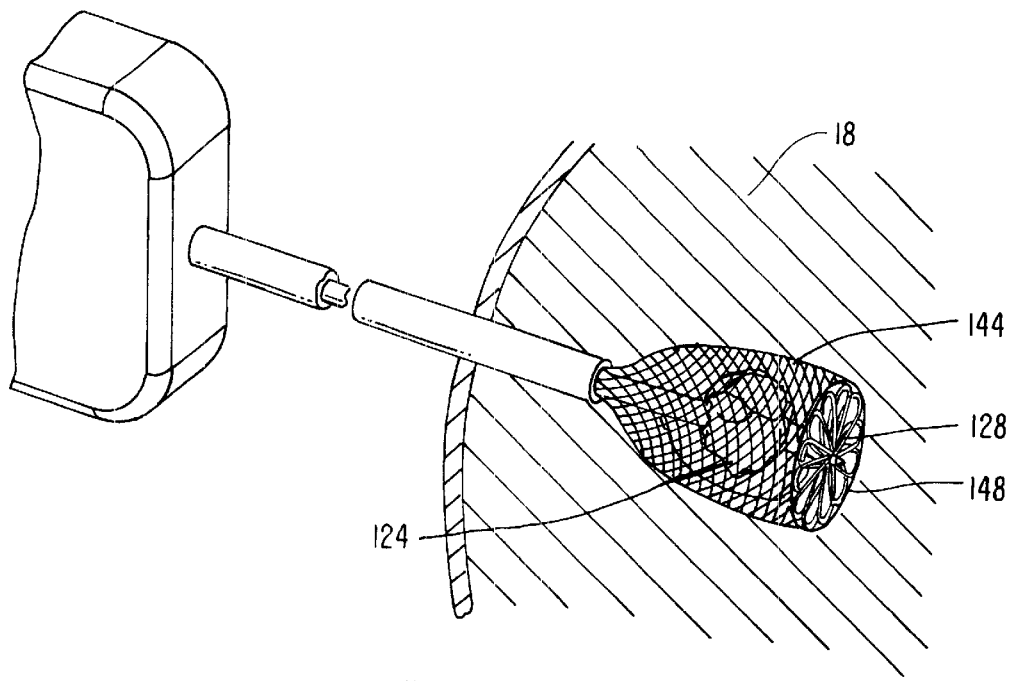
Figure 11H:
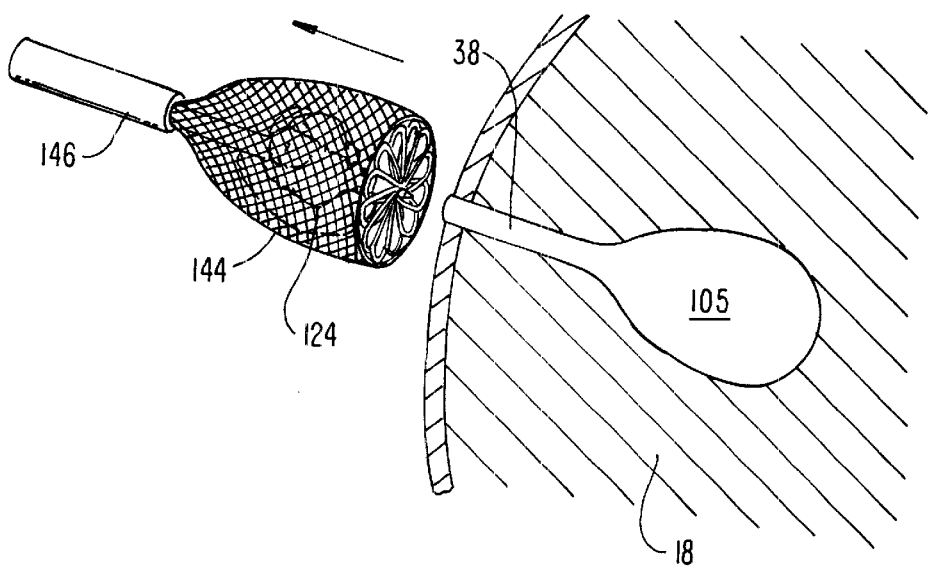

A further intraoperative tissue treatment method using suction is disclosed in FIGS. 11A–11H. FIG. 11A illustrates a suction device 120 passing through skin surface 20. Device 120 has a tubular body 121 with suction inlets 122 at its distal end, the suction inlets positioned within void 90. Fluid, typically including liquid, gas and the occasional particles, is withdrawn through suction inlets 122 so to collapse tissue 18 surrounding void 90 to create collapsed tissue 124 at target site 26 as shown in FIG. 11B. Suction device 120 has, in this embodiment, a radially expandable blocking element 126 at the distal end of body 121. Blocking element 126, in this embodiment, comprises numerous individual wires 128 which can be directed out through openings 130 formed at the distal end of tubular body 121. Blocking element 126 is positioned distally of collapsed tissue 124 at target site 26. A tissue separator assembly 132, see FIGS. 11C–11E, includes a rotatable tube 134 which passes over shaft 121 until its distal end 136 extends between collapsed tissue 124 and blocking element 126. Once in position, a wire tissue cutter 138 extends radially outwardly as indicated by an arrow 140 of FIG. 11B; tube 134 is then rotated as indicated by arrow 142 so to cut a layer of tissue 100 surrounding target site 26. To help preserve the integrity of tissue layer 100 during and subsequent to the removal of the tissue layer from the patient, a radially expandable, tubular mesh material 144 is extended out from between an outer tube 146 and rotatable tube 134 of assembly 132. Mesh material 144 may be constructed similarly to the material described with regard to FIGS. 9A–9D so that it tends to expand radially outwardly when placed under compression. The outer edge 148 of mesh material 144 tends to follow the dissection plane between the outer surface 103 of tissue layer 100 and the surrounding tissue 18. Once in the position of FIG. 11G, with outer edge 148 adjacent to blocking element 126, assembly 132 and tissue layer 100 housed within mesh material 144 can be removed in unison as indicated in FIG. 11H with tissue layer 100 substantially intact for subsequent examination.

FIGS. 7H and 11H each show an enlarged void 105 and a relatively narrow tissue tract 38. The tissue 18 is quite elastic and very often permits the removal of an enlarged mass along a relatively narrow tissue tract, after which the elastic nature of the tissue tends to cause the tissue to return to its prestretched condition. If desired, a second, enlarged expandable element 94 may be placed in the enlarged void 105. If the outer surface 103 of tissue layer 100 is found to contain diseased tissue, a second excisional procedure as described above or some other therapeutic procedure, may be accomplished if considered necessary or desirable. If outer surface 103 is found not to contain diseased tissue, enlarged void 105 may have a hemostatic, bioabsorbable implant inserted into the void; in some situations it may be desired to place a flexible implant 116 into void 105, especially while sheath 5 is maintained in place.

Figure 12A:
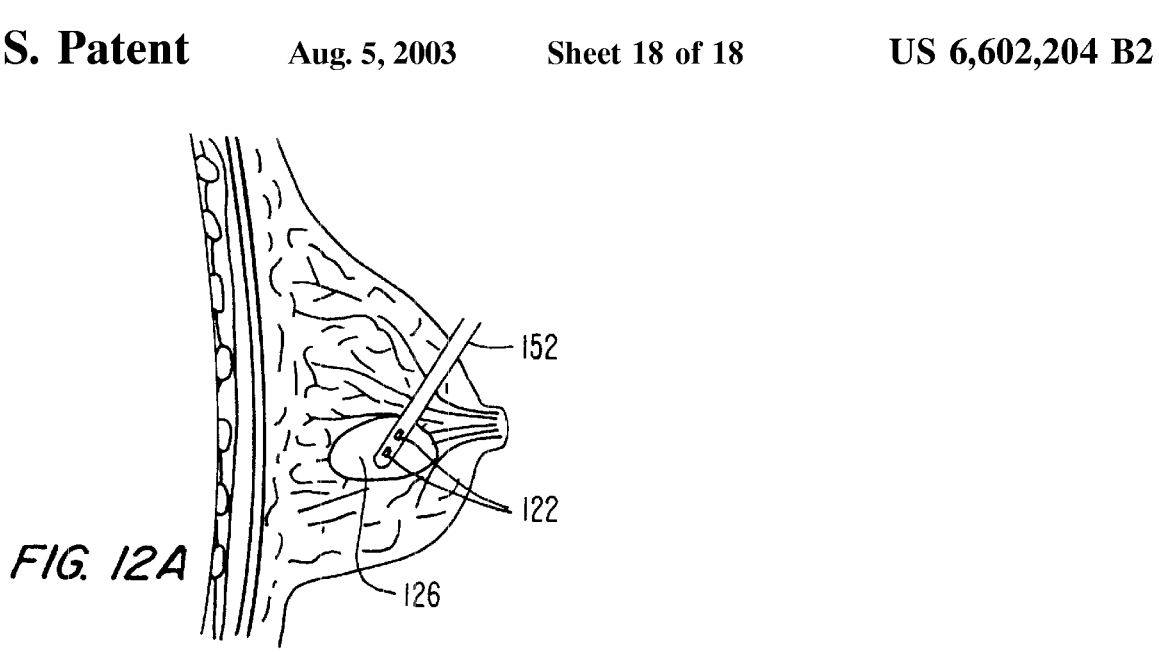
FIGS. 12A–12C illustrates an alternative to the method illustrated in FIGS. 11A–11H in which after the tissue has been collapsed using the suction device, as shown in FIG. 12B, a cutter element, such as illustrated in one or more of the above embodiments, is used to separate a layer of tissue surrounding the suction inlet of the suction device for removal from the patient.
Figure 12B:
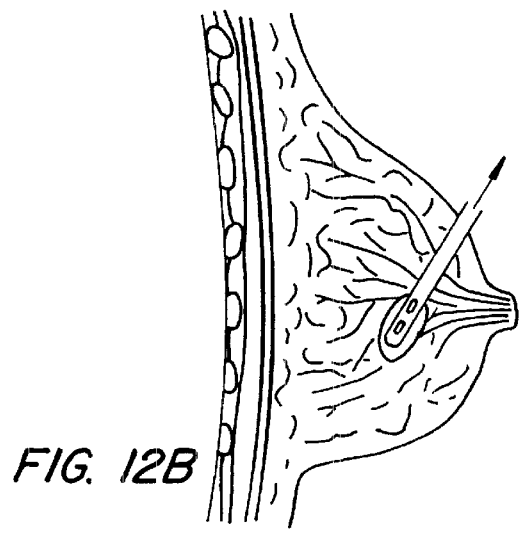
Figure 12C:
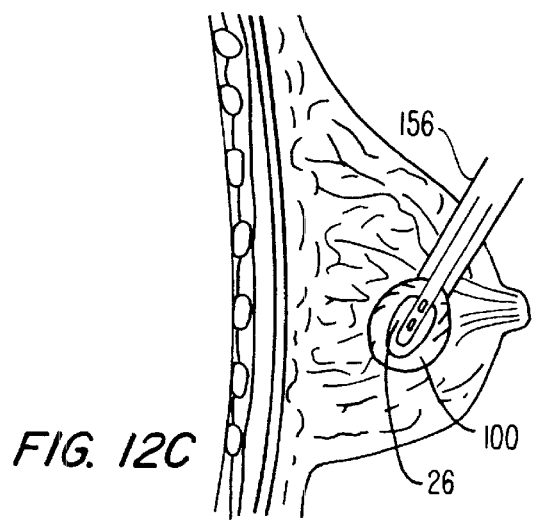

FIGS. 12A–12C show an alternative to the method of FIGS. 11A–11H. A suction device 152 extends along the tissue tract and has suction inlets 122 at its distal end. After at least partially collapsing the tissue surrounding suction inlets 122, see FIG. 12B, a rotating blade tissue cutter 156 is used to create tissue layer 100 at target site 26. Removal of tissue layer 100 can be in a manner similar to that discussed above with regard to FIGS. 3A–6C and 7A–7H.

Modification and variation can be made to the disclosed embodiments without departing from the subject of the invention as defined in the following claims. For example, blocking element 126 and/or mesh material 144, as well as other structure, may be used to remove tissue surrounding an expanded expandable element 94. The methods and devices of FIGS. 7A–9D may be used to remove collapsed tissue 124 of FIGS. 11B–11H. In some situations it may be necessary or desirable to temporarily enlarge tissue tract 38, such as using the devices and methods of FIGS. 3A–6C.

Any and all patents, patents applications and printed publications referred to above are hereby incorporated by reference.

What is claimed is:

1. An intraoperative tissue treatment method, for use following the removal of target tissue from a target site leaving access to the target site, comprising:
   introducing an expandable element into a void at a target site;
   expanding the expandable element to at least substantially fill the void;
   determining whether adequate target tissue at the target site was removed; and
   if the results of the determining step is no, then:
      separating additional tissue, at least partially surrounding the expanded element, from surrounding tissue;
      the separating step comprising rotating a cutter around the expanded element; and
      removing the additional tissue and the expanded element from the patient.

2. The method according to claim 1 wherein the introducing step is carried out before the determining step.

3. The method according to claim 1 wherein the determining step is carried out with the target tissue being diseased tissue.

4. The method according to claim 1 wherein the introducing step is carried out using at least one of a balloon, an expandable mesh and a malecot-type element as the expandable element.

5. The method according to claim 1 wherein the introducing step is carried out with the target site being within a patient's breast.

6. The method according to claim 1 wherein the introducing step is carried out through a hollow sheath.

7. The method according to claim 1 wherein the expanding step is carried out so that the expanded element at least substantially fills the void.

8. The method according to claim 1 wherein said separating step is carried out so said additional tissue completely surrounds said expanded element.

9. The method according to claim 1 wherein the removing step creates an expanded void at the body site, and further comprising introducing a second expandable element into the expanded void and expanding the second expandable element within the expanded void.

10. The method according to claim 9 wherein the introducing steps are carried out using two separate expandable elements.

11. An intraoperative tissue treatment method, for use following the removal of target tissue from a target site leaving access to the target site, comprising:
   introducing an expandable element into a void at a target site;
   expanding the expandable element to at least substantially fill the void;
   determining whether adequate target tissue at the target site was removed; and
   if the results of the determining step is no, then:
      separating additional tissue, at least partially surrounding the expanded element, from surrounding tissue using a blade which passes about the expanded element; and
      removing the additional tissue and the expanded element from the patient.

12. An intraoperative tissue treatment method, for use following the removal of target tissue from a target site leaving access to the target site, comprising:
- introducing an expandable element into a void at a target site;
- expanding the expandable element to at least substantially fill the void;
- determining whether adequate target tissue at the target site was removed; and
- if the results of the determining step is no, then:
  - separating additional tissue, at least partially surrounding the expanded element, from surrounding tissue, said additional tissue comprising an inner, at least partially void-defining surface and an outer surface; and
  - removing the additional tissue and the expanded element from the patient.

13. An intraoperative tissue treatment method, for use following the removal of target tissue from a target site leaving access to the target site, comprising:
- introducing an expandable element into a void at a target site;
- expanding the expandable element to at least substantially fill the void;
- determining whether adequate target tissue at the target site was removed; and
- if the results of the determining step is no, then:
  - separating additional tissue, at least partially surrounding the expanded element, from surrounding tissue;
  - the separating step comprising extending an expandable and contractible cutting loop at least partially over the expanded element; and
  - removing the additional tissue and the expanded element from the patient.

14. An intraoperative tissue treatment method, for use following the removal of target tissue from a target site leaving access to the target site, comprising:
- introducing an expandable element into a void at a target site;
- expanding the expandable element to at least substantially fill the void;
- determining whether adequate target tissue at the target site was removed; and
- if the results of the determining step is no, then:
  - separating additional tissue, at least partially surrounding the expanded element, from surrounding tissue;
  - the separating step comprising extending a tubular mesh cutter, having a radially expandable and contractible distal cutting end, over the expanded element; and
  - removing the additional tissue and the expanded element from the patient.

15. An intraoperative tissue treatment method, for use following the removal of target tissue from a target site leaving access to the target site, comprising:
- introducing an expandable element into a void at a target site;
- expanding the expandable element to at least substantially fill the void;
- determining whether adequate target tissue at the target site was removed; and
- if the results of the determining step is no, then:
  - substantially simultaneously removing additional tissue, at least partially surrounding the expanded element, and the expanded element from the patient.

16. An intraoperative tissue treatment method, for use following the removal of diseased tissue from a target site within a patient's breast leaving access to the target site, comprising:
- introducing an expandable element into a void at a target site;
- expanding the expandable element to at least substantially fill the void;
- determining whether all diseased tissue at the target site was removed; and
- if the results of the determining step is no, then:
  - separating a layer of tissue at least substantially surrounding the expanded element so said layer of tissue comprises an inner, a void-defining surface and an outer surface;
  - removing the separated layer of tissue, together with the expanded element, from the patient while maintaining said separated layer of tissue in a substantially intact form; and
  - inspecting the outer surface for evidence of said diseased tissue.

17. The method according to claim 16 wherein the separating and removing steps are carried out so that said layer of tissue is in at most three sections.

18. An intraoperative tissue treatment method, for use following the removal of target tissue from a target site leaving a void at the target site, comprising:
- locating a suction inlet of a suction device in fluid communication with a void at the target site;
- withdrawing fluid through the suction inlet thereby at least partially collapsing the tissue defining the void;
- determining whether all target tissue at the target site was removed;
- if the results of the determining step is no, then:
  - removing at least a portion of the collapsed tissue from the patient.

19. The method according to claim 18 wherein the locating step is carried out before the determining step.

20. The method according to claim 18 wherein the fluid withdrawing step is carried out to withdraw at least liquid and gas through the suction inlet.

21. The method according to claim 18 further comprising positioning a blocking element at a position distal of the target site.

22. The method according to claim 21 wherein the blocking element is removed during the removing step.

23. The method according to claim 18 wherein the removing step comprises removing the suction device from the patient generally simultaneously with the collapsed tissue portion.

24. The method according to claim 18 wherein the removing step comprises passing a tissue separator through tissue surrounding the target site thereby separating said portion of said collapsed tissue surrounding the target site from surrounding tissue.

25. The method according to claim 24 wherein the removing step comprises passing a radially expandable, tubular mesh material between the collapsed tissue portion and the surrounding tissue.

26. The method according to claim 18 wherein the removing step comprises:
- separating said collapsed tissue portion from surrounding tissue, the separating step being carried out so said collapsed tissue portion comprises an outer surface;
- maintaining said separated collapsed tissue portion in a substantially intact form; and further comprising:

inspecting the outer surface for evidence of said target tissue.

27. An intraoperative tissue treatment method, for use following the removal of target tissue from a target site leaving a void at the target site, comprising:
- positioning a blocking element at a position distal of the target site, the positioning step being carried out with a radially expandable mesh device as the blocking element;
- locating a suction inlet of a suction device in fluid communication with a void at the target site;
- withdrawing fluid through the suction inlet thereby at least partially collapsing the tissue defining the void;
- determining whether all target tissue at the target site was removed;
- if the results of the determining step is no, then:
  - removing at least a portion of the collapsed tissue from the patient.

28. An intraoperative tissue treatment method, for use following the removal of diseased tissue from a target site within a patient's breast leaving a void at the target site, comprising:
- locating a suction inlet of a suction device within a void at the target site;
- positioning a blocking element at a position distal of the target site;
- withdrawing fluid through the suction inlet thereby at least partially collapsing the tissue defining the void;
- determining whether all diseased tissue at the target site was removed with the excised tissue; and
- if the results of the determining step is no, then:
  - passing a tissue separator through tissue surrounding the target site thereby separating at least a portion of the collapsed tissue, comprising an outer surface, at least partially surrounding the target site from surrounding tissue;
  - passing a radially expandable, tubular mesh material between the collapsed tissue portion and the surrounding tissue;
  - removing the collapsed tissue portion, the blocking element, the tissue cutter and the tubular mesh material from the patient while maintaining said collapsed tissue portion in a substantially intact form; and
  - inspecting the outer surface for evidence of said diseased tissue.

29. The method according to claim 28 wherein the removing step is carried out to generally simultaneously remove the collapsed tissue portion, the blocking element, the tissue cutter and the tubular mesh material from the patient.

30. An intraoperative tissue treatment method, for use following the removal of tissue from a target site leaving a void at the target site and a sheath at least part way along a passageway from a region external of the patient to a void at a target site, comprising:
- maintaining the sheath at least part way along the passageway from the region external of the patient to the void at the target site;
- passing a generally flexible bag-type implant though the sheath and into the void;
- at least partially filling the void with the implant; and
- removing the sheath from the patient.

31. The method according to claim 30 wherein the maintaining step is carried out with the sheath extending into the void.

32. The method according to claim 30 wherein the passing step is carried out using a bioabsorbable implant.

33. The method according to claim 30 wherein said filling step is carried out without the addition of material into the implant once it is within the void.

34. The method according to claim 30 wherein said filling step is carried out so to at least substantially fill the void.

35. The method according to claim 30 wherein the passing step is carried out using a non-bioabsorbable implant.

* * * * *